US012703870B2

(12) United States Patent
Yao et al.

(10) Patent No.: US 12,703,870 B2
(45) Date of Patent: Aug. 11, 2026

(54) REGULATION OF ROOT DEVELOPMENT

(71) Applicant: UT-Battelle, LLC, Oak Ridge, TN (US)

(72) Inventors: Tao Yao, Oak Ridge, TN (US); Jin-Gui Chen, Oak Ridge, TN (US); Wellington Muchero, Oak Ridge, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 0 days.

(21) Appl. No.: 18/667,301

(22) Filed: May 17, 2024

(65) Prior Publication Data

US 2024/0384282 A1 Nov. 21, 2024

Related U.S. Application Data

(60) Provisional application No. 63/467,630, filed on May 19, 2023.

(51) Int. Cl.
*C12N 15/82* (2006.01)

(52) U.S. Cl.
CPC ................................ *C12N 15/8227* (2013.01)

(58) Field of Classification Search
None
See application file for complete search history.

(56) References Cited

U.S. PATENT DOCUMENTS

| | | | |
|---|---|---|---|
| 5,204,253 A | 4/1993 | Sanford et al. |
| 5,538,880 A | 7/1996 | Lundquist et al. |
| 6,013,863 A | 1/2000 | Lundquist et al. |
| 6,329,571 B1 | 12/2001 | Hiei |

OTHER PUBLICATIONS

Arai-Sanoh et al., Deep rooting conferred by Deeper Rooting 1 enhances rice yield in paddy fields, 2014, Scientific Reports, 4: 5563 (Year: 2014).*
Amack et al. (CaMV35S promoter—A plant biology and biotechnology workhorse in the era of synthetic biology, 2020, Current Plant Biology, 24:100179 (Year: 2020).*
Bannoud et al., Adventitious Rooting in *Populus* Species: Update and Perspectives, 2021, Front. Plant Sci., 12:668837 (Year: 2021).*
Gelvin et al., Integration of Agrobacterium T-DNAinto the Plant Genome, 2017, Annu. Rev. Genet. 2017. 51:195â217 (Year: 2017).*
GenBank Accession: KAJ6898587.1 (published on Mar. 16, 2023) (Year: 2023).*
Han et al., Jasmonate-regulated root growth inhibition and root hair elongation, Journal of Experimental Botany, 74:1176â1185 (Year: 2022).*
Nodzon et al., The ubiquitin ligase XBAT32 regulates lateral root development in *Arabidopsis*, 2004, The Plant Journal, 40:996-1006 (Year: 2004).*
Steffens et al., The Physiology of Adventitious Roots, 2016, Plant Physiology, vol. 170:603-617 (Year: 2006).*
Van Wees et al., Enhancement of induced disease resistance by simultaneous activation of salicylate- and jasmonate-dependent defense pathways in *Arabidopsis thaliana*, 2020, PNAS, 97:8711-8716 (Year: 2020).*
Wixon, J., *Arabidopsis thaliana*, 2001Comp. Funct. Genom., 2: 91-98. (Year: 2001).*
Chen et al., Chromosome-level genome assembly of a triploid poplar Populus alba âBerolinensis, 2023, Mol Ecol Resour., 23:1092-1107. (Year: 2023).*
Ge et al., Genomics, expression, and function analyses of XB3 family genes in cotton, 2021, Genomics 113:245-256. (Year: 2021).*
Sauter, M., Root responses to flooding, Current Opinion in Plant Biology, 2013, 16:282-286 (Year: 2013).*
Alexa, A., et al., "Improved scoring of functional groups from gene expression data by decorrelating GO graph structure", Bioinformatics 2006, pp. 1600-1607, vol. 22, No. 13.
Bannoud, F., et al., "Adventitious Rooting in *Populus* Species: Update and Perspectives", Frontiers in Plant Science, May 2021, pp. 1-22, vol. 12, Article 668837.
Bellini, C., et al., "Adventitious Roots and Lateral Roots: Similarities and Differences", ARI, Jan. 31, 2014, pp. 17:1-17:9 ask inventors for final version?
Buer, C.S., et al., "Ethylene Modulates Flavonoid Accumulation and Gravitropic Responses in Roots of *Arabidopsis*", Plant Physiology, Apr. 2006, pp. 1384-1396, vol. 140.
Carvalho, S.D., et al., "XBAT35, a Novel *Arabidopsis* Ring E3 Ligase Exhibiting Dual Targeting of Its Splice Isoforms, Is Involved in Ethylene-Mediated Regulation of Apical Hook Curvature", Molecular Plant, Nov. 2012, pp. 1295-1309, vol. 5, No. 6.
Cerdan, P.D., et al., "A 146 bp fragment of the tobacco Lhcb1*2 promoter confers very-low-fluence, low-fluence and high-irradiance responses of phytochrome to a minimal CaMV 35S promoter", Plant Molecular Biology, 1997, pp. 245-255.
Chang, S.H., et al., "Enhancement of plant formation from embryo cultures of Taxus mairei using suitable culture medium and PVP", Bot. Bull. Acad. Sin., (1996), pp. 35-40, 37.
Constabel, C.P., "Molecular Controls of Proanthocyanidin Synthesis and Structure: Prospects for Genetic Engineering in Crop Plants", J. Agric. Food Chem. 2018, pp. 9882-9888, 66.
Csukasi, F., et al., "Modification of plant hormone levels and signaling as a tool in plant biotechnology", Biotechnol. J. 2009, pp. 1293-1304, 4.
De Almedia, M.R., et al., "Environmental control of adventitious rooting in Eucalyptus and Populus cuttings", Trees (2017) pp. 1377-1390, 31.

(Continued)

*Primary Examiner* — Bratislav Stankovic
*Assistant Examiner* — Jay Chatterjee
(74) *Attorney, Agent, or Firm* — Scully, Scott, Murphy & Presser, P.C.

(57) ABSTRACT

The present disclosure provides methods to genetically engineer plants by manipulating the expression of the PtrXB38 polypeptide to increase root development. Also provided are genetically engineer plants that can be obtained by the methods according to the present disclosure.

35 Claims, 25 Drawing Sheets
(20 of 25 Drawing Sheet(s) Filed in Color)

Specification includes a Sequence Listing.

(56) References Cited

OTHER PUBLICATIONS

Depuydt, S., et al., "Hormone Signalling Crosstalk in Plant Growth Review Regulation", Current Biology, May 10, 2011, pp. R365-R373, 21.
Diaz-Sala, C., et al., "A Perspective on Adventitious Root Formation in Tree Species", Plants 2020, pp. 1-8, 9, 1789.
Dobin, A., et al., "Star: ultrafast universal RNA-seq aligner", Bioinformatics, 2013, pp. 15-21, vol. 29, No. 1.
Druege, U., et al., "Plant Hormone Homeostasis, Signaling, and Function during Adventitious Root Formation in Cuttings", Frontiers in Plant Science, Mar. 2016, pp. 1-14, vol. 7, Article 381.
Fejes, E., et al., "A 268 bp upstream sequence mediates the circadian clock-regulated transcription of the wheat Cab-1 gene in transgenic plants", Plant Molecular Biology, 1990, pp. 921-932, 15.
Fromm, H., et al., "An Octopine Synthase Enhancer Element Directs Tissue-Specific Expression and Binds ASF-1, a Factor from Tobacco Nuclear Extracts", The Plant Cell, Oct. 1989, pp. 977-984, vol. 1.
Jacobs, T.B., et al., "Targeted genome modifications in soybean with CRISPR/Cas9", BMC Biotechnology (2015), pp. 1-10, 15:16.
Ke, S.-W., et al., "Ethylene signaling modulates contents of catechin and ability of antioxidant in Camellia sinensis", Botanical Studies (2018), pp. 1-8, 59:11.
Labbe, J., et al., "Mediation of plant-mycorrhizal interaction by a lectin receptor-like kinase", Nature Plants, Jul. 2019, pp. 676-680, vol. 5.
Lakehal, A., et al., "Control of adventitious root formation: insights into synergistic and antagonistic hormonal interactions", Physiologia Plantarum, 2019, pp. 90-100, 165.
Li, C., et al., "*Arabidopsis* TCP20 links regulation of growth and cell division control pathways", PNAS, Sep. 6, 2005, pp. 12978-12983, vol. 102, No. 36.
Li, J., et al., "The WUSCHEL-related homeobox 5a (PtoWOX5a) is involved in adventitious root development in poplar", Tree Physiology, 2017, pp. 1-15, vol. 00.
Li, Q., et al., "*Arabidopsis* Ring-type E3 ubiquitin ligase XBAT35.2 promotes proteasome-dependent degradation of ACD11 to attenuate abiotic stress tolerance", The Plant Journal (2020), pp. 1712-1723, 104.
Li, S.-W., et al., "Molecular Bases for the Regulation of Adventitious Root Generation in Plants", Frontiers in Plant Science, Jan. 2021, pp. 1-19, vol. 12, Article 614072.
Liu, H., et al., "The Ring-Type E3 Ligase XBAT35.2 Is Involved in Cell Death Induction and Pathogen Response", Plant Physiology, Nov. 2017, pp. 1469-1483, vol. 175.
Love, M., et al., "Moderated estimation of fold change and dispersion for RNA-seq data with DESeq2", Genome Biology (2014), pp. 1-21, 15:550.
Luan, S., et al., "A Rice cab Gene Promoter Contains Separate cis-Acting Elements That Regulate Expression in Dicot and Monocot Plants", The Plant Cell, Aug. 1992, pp. 971-981, vol. 4.
Lübberstedt, T., et al., "Promoters from Genes for Plastid Proteins Possess Regions with Different Sensitivities toward Red and Blue Light", Plant Physiol. (1994), pp. 997-1006, 104.
Lyzenga, W.J., et al., "The *Arabidopsis* Ring-type E3 ligase XBAT32 mediates the proteasomal degradation of the ethylene biosynthetic enzyme, 1-aminocyclopropane-1-carboxylate synthase 7", The Plant Journal (2012), pp. 23-34, 71.
Ma, W., et al., "Melatonin alters the secondary metabolite profile of grape berry skin by promoting VvMYB14-mediated ethylene biosynthesis", Horticulture Research (2021), pp. 1-15, 8:43.
Matsuoka, M., et al., "Tissue-specific light-regulated expression directed by the promoter of a C4 gene, maize pyruvate, orthophosphate dikinase, in a C3 plant, rice", Proc. Natl. Acad. Sci. USA, Oct. 1993, pp. 9586-9590, vol. 90.
Miller, A.J., et al., "From forest to field: Perennial fruit crop domestication", American Journal of Botany, 2011, pp. 1389-1414, 98(9).
Motte, H., et al., "Molecular and Environmental Regulation of Root Development", Annual Review of Plant Biology, 2019, pp. 465-488, 70.
Muchero, W., et al., "Association mapping, transcriptomics, and transient expression identify candidate genes mediating plant-pathogen interactions in a tree", PNAS, Nov. 6, 2018, pp. 11573-11578, vol. 115, No. 45.
Muday, G.K., et al., "Auxin and ethylene: collaborators or competitors?", Trends in Plant Science Apr. 2012, pp. 181-195, vol. 17, No. 4.
Niu, W., et al., "Factors affecting Agrobacterium tumefaciens-mediated transformation of peppermint", Plant Cell Reports (2000), pp. 304-310, 19.
Prasad, M.E., et al., "*Arabidopsis* Ring E3 Ligase XBAT32 Regulates Lateral Root Production through Its Role in Ethylene Biosynthesis", Plant Physiology, Aug. 2010, pp. 1587-1596, vol. 153.
Qin, H., et al., "Auxin Controlled by Ethylene Steers Root Development", International Journal of Molecular Sciences, 2018, pp. 1-13, 19, 3656.
Ramirez-Parra, E., et al., "The transcription factor OBP4 controls root growth and promotes callus formation", New Phytologist (2017), pp. 1787-1801, 213.
Rigal, A., et al., "The Aintegumenta Like1 Homeotic Transcription Factor PtAIL1 Controls the Formation of Adventitious Root Primordia in Poplar", Plant Physiology, Dec. 2012, pp. 1996-2006, vol. 160.
Rogers, E.D., et al., "Regulation of plant root system architecture: implications for crop advancement", Current Opinion in Biotechnology 2015, pp. 93-98, 32.
Schwacke, R., et al., "MapMan4: A Refined Protein Classification and Annotation Framework Applicable to Multi-Omics Data Analysis", Molecular Plant, Jun. 2019, pp. 879-892, 12.
Song, Y., et al., "Miniature inverted repeat transposable elements cis-regulate circular RNA expression and promote ethylene biosynthesis, reducing heat tolerance in Populus tomentosa", Journal of Experimental Botany, 2021, pp. 1978-1994, vol. 72, No. 5.
Sun, P., et al., "Deciphering Genetic Architecture of Adventitious Root and Related Shoot Traits in Populus Using QTL Mapping and RNA-Seq Data", Int. J. Mol. Sci. 2019, pp. 1-22, 20, 6114.
Ten Hove, C.A., et al., "Schizoriza Encodes a Nuclear Factor Regulating Asymmetry of Stem Cell Divisions in the *Arabidopsis* Root", Current Biology, Mar. 9, 2010, pp. 452-457, 20.
Truernit, E., et al., "The promoter of the *Arabidopsis thaliana* SUC2 sucrose-H+ symporter gene directs expression of p-glucuronidase to the phloem: Evidence for phloem loading and unloading by SUC2", Planta (1995), pp. 564-570, 196.
Trupiano, D., et al., "Identification, characterization of an AP2/ERF transcription factor that promotes adventitious, lateral root formation in Populus", Planta, 2013, 12 pages.
Tsai, C.-J., et al., "Compensatory Guaiacyl Lignin Biosynthesis at the Expense of Syringyl Lignin in 4CL1-Knockout Poplar", Plant Physiology, May 2020, pp. 123-136, vol. 183.
Tschaplinski, T.J., et al., "Down-regulation of the caffeic acid O-methyltransferase gene in switchgrass reveals a novel monolignol analog", Biotechnology for Biofuels 2012, pp. 1-15, 5:71.
Tuskan, G.A., et al., "The Genome of Black Cottonwood, *Populus trichocarpa* (Torr. & Gray)", Science, Sep. 15, 2006, pp. 1596-1604, vol. 313.
Ullah, C., et al., "Salicylic acid activates poplar defense against the biotrophic rust fungus *Melampsora larici-populina* via increased biosynthesis of catechin and proanthocyanidins", New Phytologist (2019), pp. 960-975, 221.
Wang, J., et al., "Formation, characterization and modeling of emergent synthetic microbial communities", Computational and Structural Biotechnology Journal (2021), pp. 1917-1927, 19.
Xie, C,, et al., "Kobas 2.0: a web server for annotation and identification of enriched pathways and diseases", Nucleic Acids Research, 2011, pp. W316-W322, vol. 39, Web Server issue.
Xu, W., et al., "Transcriptional control of flavonoid biosynthesis by MYB-bHLH-WDR complexes", Trends in Plant Science, Mar. 2015, pp. 176-185, vol. 20, No. 3.
Xuan, L., et al., "Identification and characterization of three PeSHRs and one PeSCR involved in adventitious root development of Populus", Plant Cell Tiss Organ Cult (2014), pp. 253-264, 117.

(56) References Cited

OTHER PUBLICATIONS

Yao, T., et al., "Expression quantitative trait loci mapping identified PtrXB38 as a key hub gene in adventitious root development in Populus", New Phytologist (2023), pp. 1-17.
Yamamoto, N., et al., "The Promoter of a Pine Photosynthetic Gene Allows Expression of a β-Glucuronidase Reporter Gene in Transgenic Rice Plants in a Light-Independent but Tissue-Specific Manner", Plant Cell Physiol., (1994), pp. 773-778, 35(5).
Yates, T.B., et al., "The Ancient Salicoid Genome Duplication Event: A Platform for Reconstruction of De Novo Gene Evolution in Populus trichocarpa", Genome Biol. Evol., 2021, pp. 1-14, 13(9).
Yu, F., et al., "ESCRT-I Component VPS23A Is Targeted by E3 Ubiquitin Ligase XBAT35 for Proteasome-Mediated Degradation in Modulating ABA Signaling", Molecular Plant, Nov. 2, 2020, pp. 1556-1569, 13.
Zhang, J., et al., "Genome-wide association studies and expression-based quantitative trait loci analyses reveal roles of HCT2 in caffeoylquinic acid biosynthesis and its regulation by defense-responsive transcription factors in Populus", New Phytologist (2018), pp. 502-516, 220.
Zhang, J., et al., "Transcriptional regulatory framework for vascular cambium development in *Arabidopsis* roots", Nature Plants, Oct. 2019, pp. 1033-1042, vol. 5.
Zhou, X., et al., "Genome-wide efficient mixed-model analysis for association studies", Nature Genetics, Jul. 2012, pp. 821-826, vol. 44, No. 7.

* cited by examiner

3A

| Gene model | OE-72 | OE-22 | Gene symbol |
|---|---|---|---|
| Potri.002G207400 | 1.55 | 1.89 | YUC10 |
| Potri.004G220100 | 1.3 | 1.09 | ARF15 |
| Potri.013G087000 | 3.99 | 4.06 | PIN5 |
| Potri.013G144300 | 2.31 | 4.32 | GH3.10 |
| Potri.003G161300 | 2.39 | 1.65 | GH3.17 |
| Potri.007G067800 | 1.92 | 1.38 | SAUR-like auxin-responsive protein |
| Potri.009G126000 | 1.46 | 2.31 | SAUR-like auxin-responsive protein |
| Potri.009G127500 | 4.53 | 4.02 | SAUR-like auxin-responsive protein |
| Potri.009G127600 | 5.88 | 6.58 | SAUR-like auxin-responsive protein |
| Potri.010G224500 | 5.84 | 6.11 | SAUR-like auxin-responsive protein |
| Potri.002G057500 | -1.61 | 2.08 | SAUR-like auxin-responsive protein |

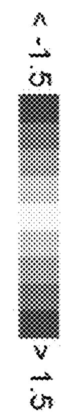

3B

| Protein model | OE-72 | OE-22 | Protein symbol |
|---|---|---|---|
| Potri.011G091900 | 4.72 | 4.02 | ARF6 |
| Potri.006G077800 | 4.85 | 4.38 | ARF7 |
| Potri.005G207700 | 5.16 | 4.65 | ARF8 |
| Potri.001G358500 | 5.46 | 4.91 | ARF8 |
| Potri.002G055000 | 5.39 | 5.01 | ARF8 |

3C

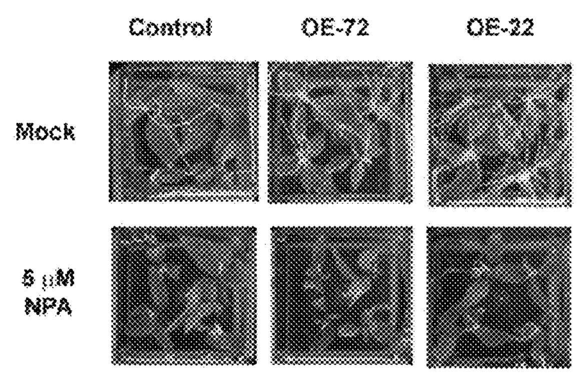

3D

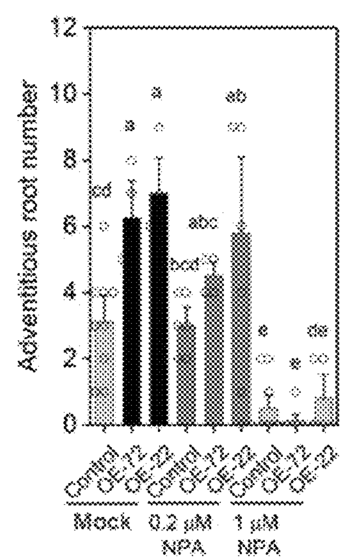

| Gene model | OE-72 | OE-22 | Gene symbol |
|---|---|---|---|
| Potri.013G004100 | -0.46 | -0.59 | SAMS3 |
| Potri.006G123200 | -0.35 | 0.14 | MAT3 |
| Potri.002G189000 | -0.6 | -0.33 | SAM2 |
| Potri.002G189200 | -0.28 | -0.08 | SAM2 |
| Potri.008G099300 | -0.42 | -0.02 | SAMS3 |
| Potri.007G007800 | 2.24 | 0.9 | ACS3 |
| Potri.006G151600 | 2.54 | 1.75 | ACO1 |
| Potri.011G020900 | 2.39 | 1.4 | ACO4 |
| Potri.002G224100 | -0.43 | -0.74 | ACO4 |
| Potri.004G003000 | 0.04 | -0.98 | ACO4 |
| Potri.002G078600 | -0.86 | -0.77 | ACO5 |
| Potri.005G182700 | -0.81 | -0.17 | ACO5 |

4B

| Protein model | OE-72 | OE-22 | Protein symbol |
|---|---|---|---|
| Potri.013G004100 | 1.52 | 2.11 | SAMS3 |
| Potri.006G123200 | 1.49 | 2.13 | MAT3 |
| Potri.002G189000 | 1.66 | 2.25 | SAM2 |
| Potri.002G189200 | 1.66 | 2.25 | SAM2 |
| Potri.008G099300 | 1.73 | 2.36 | SAMS3 |
| Potri.006G151600 | 8.24 | 9.87 | ACO1 |
| Potri.011G020900 | 2.28 | 1.11 | ACO4 |
| Potri.002G224100 | -0.6 | -1.33 | ACO4 |
| Potri.004G003000 | 0.1 | -1.03 | ACO4 |
| Potri.002G078600 | 6.61 | 7.63 | ACO5 |
| Potri.005G182700 | 0.75 | 1.71 | ACO5 |

| Gene model | OE-72 | OE-22 | Gene symbol |
|---|---|---|---|
| Potri.003G080600 | 1.45 | 2.63 | ERF3 |
| Potri.003G150700 | 1.56 | 1.69 | ERF13 |
| Potri.010G072400 | 2.77 | -1.94 | ERF19 |
| Potri.005G223200 | 1.38 | 0.81 | ERF32 |
| Potri.010G072300 | 1.72 | 1.37 | ERF33 |
| Potri.002G201600 | 1.42 | 2.37 | ERF36 |
| Potri.014G126100 | 0.96 | 1.48 | ERF37 |
| Potri.002G043300 | 2.65 | 1.56 | ERF41 |
| Potri.007G138100 | 0.55 | 0.51 | ERF45 |
| Potri.011G057000 | 0.74 | 0.82 | ERF47 |
| Potri.011G056000 | 0 | -0.01 | ERF49 |
| Potri.005G087200 | 1.95 | 2.43 | ERF74 |
| Potri.014G094500 | 1.06 | 0.73 | ERF84 |
| Potri.001G094800 | 1 | 1.84 | ERF87 |
| Potri.005G168700 | 0.33 | 0.17 | ERF113 |
| Potri.006G261200 | 0.75 | 0.77 | ERF117 |
| Potri.005G176000 | 1.35 | 1.55 | ERF130 |
| Potri.002G085600 | 1.35 | 2.38 | ERF131 |

4E

4F

5I

| Gene mode | OE-72 | OE-22 | Gene symbol |
|---|---|---|---|
| Potri.006G126800 | 0.82 | 0.61 | PAL |
| Potri.010G224200 | -0.79 | -0.28 | PAL |
| Potri.010G224100 | -0.65 | -0.1 | PAL |
| Potri.008G038200 | -0.44 | 0.13 | PAL |
| Potri.001G036900 | -0.71 | -0.33 | 4CL |
| Potri.003G188500 | -0.38 | 0.29 | 4CL |
| Potri.001G051500 | 0.06 | 0.2 | CHS |
| Potri.001G051600 | -0.17 | 0.06 | CHS |
| Potri.003G176900 | -0.03 | 0.13 | CHS |
| Potri.003G176800 | 0.25 | 0.4 | CHS |
| Potri.003G176700 | 0.27 | 0.34 | CHS |
| Potri.005G113900 | -0.02 | 0.19 | F3H |
| Potri.005G114000 | 0.1 | 0.29 | F3H |
| Potri.005G113700 | -0.17 | 0.02 | F3H |
| Potri.004G139700 | 0.37 | 0.04 | FLS |
| Potri.001G113100 | -0.05 | -0.07 | ANS |
| Potri.003G119100 | -0.29 | -0.1 | ANS |

5J

| Protein mode | OE-72 | OE-22 | Protein symbol |
|---|---|---|---|
| Potri.006G126800 | 1.14 | 1.64 | PAL |
| Potri.010G224200 | 1.32 | 1.81 | PAL |
| Potri.010G224100 | 1.33 | 1.8 | PAL |
| Potri.008G038200 | 1.38 | 1.78 | PAL |
| Potri.001G036900 | 0.75 | 0.98 | 4CL |
| Potri.003G188500 | 0.64 | 1.3 | 4CL |
| Potri.001G051500 | 3.19 | 4.21 | CHS |
| Potri.001G051600 | 3.2 | 4.22 | CHS |
| Potri.003G176900 | 3.57 | 4.69 | CHS |
| Potri.003G176800 | 3.61 | 4.75 | CHS |
| Potri.003G176700 | 7.7 | 9.5 | CHS |
| Potri.005G113900 | 2.36 | 3.45 | F3H |
| Potri.005G114000 | 2.36 | 3.45 | F3H |
| Potri.005G113700 | 2.4 | 3.54 | F3H |
| Potri.004G139700 | 3.81 | 4.59 | FLS |
| Potri.001G113100 | 2.39 | 3.33 | ANS |
| Potri.003G119100 | 3.08 | 3.97 | ANS |

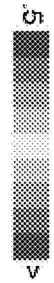

*XBAT35* Alleles

| Plant line | a1 | p1 | a2 | p2 |
|---|---|---|---|---|
| Control | WT | WT | WT | WT |
| KO-1 | +1 | +1 | +4 | -2 |
| KO-15 | +1 | +1 | +1 | +1 |
| KO-59 | +1 | +1 | +1 | +1 |

9B

10A

10B

13A

13B

16A

16B

SEQUENCE LISTING

```
Sequence total quantity: 11
SEQ ID NO: 1            moltype = DNA  length = 1431
FEATURE                 Location/Qualifiers
source                  1..1431
                        mol_type = other DNA
                        organism = Populus trichocarpa
SEQUENCE: 1
atggggcaac agcaatcaaa gcacgagttg ctgtatcagc aagtgaaaaa cggcaacata  60
gaaggaatca aaaaactttg cagagaaggc gctcgcctcg agtggattga taaagaagga  120
aaaacaccac tgatattggc gtgtttggat cctcaactct ttaacgtggc taaaactttg  180
attgagctcg gtgctgatgt taatgcctat cgcccaggtc gaaagggggg gaatcccttg  240
catcatgcgg caaaaaaagg tcttgaaaat actgtcaagt tacttctttc acatggagca  300
aatgcattaa tgacgaatga tgattgtcaa actcctctag aagttgctag ggcaaaaggg  360
tacggcaatg ttgtccgggc aattgagagt catatttgcc tattctctgg ttggttgcgg  420
gagttttatg gacctggatt tctagaagta ttggcacctc ggttggtttc aagaaacata  480
tgggctgttg ttttacctac tggttcccga aatcctggaa tgccttgcaa gttcgaactt  540
gccatttatt ctagtttgaa ggatgctaaa ccacgcacga taattgcatt gtggaaagca  600
aatctggaag aaccgaagtt tcaccgctcc gatcatactg tgatgattgc tgacaactcc  660
actaaaacac gcattaaact cgctcctgca aatgaaagag acaagcaaca gcttcagtgg  720
ttttgtgatg catgcaaagg aataccacag gtaatgcatc ctctagaatt tctgtccaga  780
tctcagaatc tggttgttca agcaactgct ccaccatcgg atgaagatcc agagatagca  840
atggcagtaa atgcctccat tcagtctgcc atggcagagc aacctatttt tgatacccac  900
tctagcactg gagcaagttc atcctctagc tggaattgcc ctgttaatga tggcggtcaa  960
ggtgctatgg atgtgccagc aacacctcct ccaaaaacaa ctagcagcgg atgggcacct  1020
tatgaaagtg tatctagtgg cagctcaact cagcaaacca agatcttgaa tagcagcgtt  1080
gctgatgtcc agacagcaac tgatgcccaa gattcagtcc catcagctcc acccattgta  1140
gatgagctta tagaagatgg tcccattcac tatccatcaa ttgattccag ccccccttgat  1200
ttttcttccc tgccccttga gaatttacca gaaaacacgg gtgaaaagaa agaagatgga  1260
ggttcatcat catgtgtaat atgtttagat gctccagttg agggagcttg cattccatgt  1320
ggccacatgg ttggatgtat gtcttgtttg aaggaaatca aagccaagga atggggttgc  1380
cctgtgtgtc gtgccacaat taaccaggtt gtaaggctct atgctgtttg a           1431

SEQ ID NO: 2            moltype = AA  length = 476
FEATURE                 Location/Qualifiers
source                  1..476
                        mol_type = protein
                        organism = Populus trichocarpa
SEQUENCE: 2
MGQQQSKHEL LYQQVKNGNI EGIKKLCREG ARLEWIDKEG KTPLILACLD PQLFNVAKTL  60
IELGADVNAY RPGRKGGNPL HHAAKKGLEN TVKLLLSHGA NALMTNDDCQ TPLEVARAKG  120
YGNVVRAIES HICLFSGWLR EFYGPGFLEV LAPRLVSRNI WAVVLPTGSR NPGMPCKFEL  180
AIYSSLKDAK PRTIIALWKA NLEEPKFHRS DHTVMIADNS TKTRIKLAPA NERDKQQLQW  240
FCDACKGIPQ VMHPLEFLSR SQNLVVQATA PPSDEDPEIA MAVNASIQSA MAEQPIFDTH  300
SSTGASSSSS WNCPVNDGGQ GAMDVPATPP PKTTSSGWAP YESVSSGSST QQTKILNSSV  360
ADVQTATDAQ DSVPSAPPIV DELIEDGPIH YPSIDSSPLD FSSLPLENLP ENTGEKKEDG  420
GSSSCVICLD APVEGACIPC GHMVGCMSCL KEIKAKEWGC PVCRATINQV VRLYAV      476

SEQ ID NO: 3            moltype = DNA  length = 7872
FEATURE                 Location/Qualifiers
source                  1..7872
                        mol_type = other DNA
                        organism = Populus trichocarpa
SEQUENCE: 3
acacaaaaca aatgacttag gatgcataaa tatttccatg ccatgatata ctgtatgtat  60
tagataatta caaactagta gaagagtatt tctgagttcc agccttgatc aagttaaaca  120
agaaaatcat tcgtcaagag gcatattatt tccaagagtt cttttccatg cgcatgtctg  180
ggaagaagaa ggtggtgttc tgctcattga tcccgtttga agcaaaggaa aggcaggggg  240
ggaatattat ttaaatttgc ccccatgcag gatcgaacta cagaccttca gtttacaaga  300
ctgccgctct accactcttg ctctctcaaa agtcaatttc gttattttat gtatgatgtc  360
ctttcgggta tctgatgagg tattatcatg ttcagaattt ttatagttga gataagtgaa  420
ttttatgtag ctttcccgga aagtaccgct ccgatttacc tctaaataat acgagaagag  480
aagagaaggc aatccaggaa ggaaggaatc cttcattttt gtttgttttg tgatacaaaa  540
agaatggggc aacagcaatc aaagcacgag ttgctgtatc agcaagtgaa aaacggcaac  600
atagaaggaa tcaaaaaact ttgcagagaa ggcgctcgcc tcgaggttcc gattattcca  660
actttttat ctctcctttt cattattttt tttaataaat ctaattggtt ttgttgtgca  720
gtggattgat aaagaaggaa aaacaccact gatattggcg tgtttggatc ctcaactctt  780
taacgtggct aaaactttga ttgagctcgg tgctgatgtt aatgcctatc gcccaggttt  840
ccctttcttt actaatttaa atattcattt gctttcttaa tttttcaatt aagagaaatt  900
agttcgttct taattagttc agtactccac tgcataacaa aacaggttca ttttcgaata  960
tattacggta aaggattttt tttttttga aggaattgcc tctgcccacg gattcttgat  1020
taacgtgtta attctgttta tgagtataat tatttttatt ttttgtatcg agctgtaggt  1080
cgaaaggggg ggaatccctt gcatcatgcg gcaaaaaaag gtcttgaaaa tactgtcaag  1140
ttacttcttt cacatggagg tgaggcgagc tcctgtactt aaagagatta gattggttgt  1200
agttattttt tatttaaaaa tttattaaaa taattatttt tgatatcaat atattaaaat  1260
aatttaaaaa cactaaaaat atattaatta aaaaaaatta aaaatgtttc aaattttttt  1320
aaaaaaggtt ttgaaatgta aaaacaaaca gataattgct tttaaaagtg atttttcttt  1380
gaaaattcat taaaacacca aaaaaaatta atttgaagca aataaaaatt taaatttttt  1440
ctaaaacaat tttaaaacgc aaaaataaat aagtaatagt tgtttttcaa aatgtttttc  1500
```

-continued

```
actcgaaaat tcataaaaat aatatttgtt taaaaaaaat atttttgata tcagtgcatc  1560
aaaatgattt caaaacacca aaaaaatatt aatttgaagc aaaaaaataa aaaaaaatta  1620
aatttttaa aacaaaaaac aaacaggtaa tagtttcttt ttaaaatgtt ttttatttga  1680
aaattcatca aaataatata tgtttttagt tttaaaaaat ttatttttga catcagcgca  1740
tcaaaatgat ttaaaaatac taaaaaaata ttaatttaaa gaaaataaaa aaaattaaat  1800
ttttaaaaaa atatttttaa aatacaaaaa agaatagtta atttttgcag ctgtgtgtgt  1860
gtctatatat atatatatat atatatatat atattggagt gtcagcgata gtttaataag  1920
tatttgtttc tttttaattt tcagcaaatg cattaatgac gaatgatgat tgtcaaactc  1980
ctctagaagt tgctagggca aaagggtacg gcaatgttgt ccgggcaatt gaggtatgct  2040
taaccgttca tgctgtgatg ttgtaactac tttgtaactg ggcaacgtgc gaaaataatt  2100
tctgttaatt accatgtaaa aaagattttt tcccctaatt ctttgcagag tcatatttgc  2160
ctattctctg gttggttgcg ggagttttat ggacctggat ttctagaagt attggcacct  2220
cggttggttt caagaaacat gtgggtattt gttgtttttt aatactactt tgtaagttat  2280
ggaatatgtt atctaggcag tttgaggttg aaaatataat tacggttatt ttttaaaatg  2340
ttttttattt aaaaatatat taaaataata ttttttttat tttttaaaaa ttatttttga  2400
tattagcgca ttaaaataat ttaaaaatat caaaaaatat taatttgaag aaaaaaataa  2460
aaaaaattca aacccttta aaacgcaaaa acaaatataa ccttagattg aaatggcttg  2520
ttgcatgtaa catttgctat acagctaaat attgttctca aaaagcactg gatttgttat  2580
gcctaatagt gtcacggctt atgcagatgg gctgttgttt tacctactgg ttcccgaaat  2640
cctggaatgc cttgcaagtt cgaacttgcc atttattcta gtttgaaggt acgccaagta  2700
aaattttcta atttgcaaga aattggatac cagattcaca ttcattgtta aaattttata  2760
acgatgcagg cttttgtttt tgtgctacct ttgaaagtta tttttggtt ctaggctctg  2820
ctgtaatgat acttgtattt gtctttaagc ttttggaatt cttgtccggc acattcctgg  2880
tttgcatcgg tggtttatct ttattcttgt ttatattata catagttatt agatatccta  2940
catgaggatt gaaccggaca agaagccggg tttagggtta tataaattga ctcggatcaa  3000
ccaaaattaa ctcggaaaaa ttaaaaaaaa tattataagt tctaatattt catataaaaa  3060
aattaaaaaa taatccatgt gaatatatgt tatacttgtt ataaataatg aagtttaaaa  3120
gattatttca aaaggttttt tatcgcatat tgaaaagata ttatgtgtta tccttttaag  3180
ttgaagtatg taaaccaaaa agacttttta tcccacattg aaaaaacata attttttct  3240
tgtgaacata aaatatatat actaaagggc ttcaaatccc acataaaaaa ataaaatatt  3300
attctagtat ttatatagtg aactttgaaa aaagttaata accaactaaa aaaaaaacgg  3360
atctcaatcg ggttttgcct ggtcaaccaa gtttttgctc atcccattct ttgtcctcac  3420
ccggaccgat ctagccatcg ggaaaccatg ctggttcatt ccgggtttaa taactatggt  3480
ttatacacat tggttggttt tctagcagtg ttatgggttt ttaccaaaaa cacactttta  3540
ttataaaatt tatctggttc tggattcata atggttgtag ctatacctgt taaccttcca  3600
tgtatttaat cgatagaatg tggtgggaaa caataaatgt tgtttggctc tacaggtgga  3660
aatatataaa agctcaggtt gagactcgaa ctaatggaat atatccctct taaaaccccg  3720
tgtgagtgcc tctacatgtg agtgagacac aaggttattg ttcctagcta ggttgaagtc  3780
tacctcatcc cacctagcac agtggcttga atcaaagata ttttattaag taatccaagc  3840
acctacagta ctgttacaag ctgctttagt ggtaaaaaaa tgctgctatt ttgctccttc  3900
tagctgtttt catggtgttg aaatagtctt caaagatgtc aatacttctt ggcattcaga  3960
aatgagaaca tcgcagcgtg ggaggtggtg atgtgcttag ctactacttc cacatccaag  4020
catgctttgc atcaattacc acttgaacat tttagtgcta gaattttgca gaataggctg  4080
cattttggaa cctctcactg tgtgctgcat gttaaaacaa agcaaacttt gtttatgaag  4140
ttgcatgaaa tgggactgac gactcacttt caacggtctc tttctttgat gatagatgtt  4200
atcagggttt tatttcttag tttagttgtc cttattcctt gtttgaattt gtattccaag  4260
tagtgtttac aaatgtaaga tgttgtatcc ctatgtttta aagtgctata ttttcttctc  4320
ttttaagtta tgactttctg gttcttggta attttcttac atattaatgg acgaccagga  4380
tgctaaacca cgcacgataa ttgcattgtg gaaagcaaat ctggaagaac cgaagtttca  4440
ccgctccgat catactgtga tgattgctga caactccact agtaatttct caatgatgat  4500
aactatctgc gtatctctta ttaacctttg ttgaagttga tgtcatgttg gtttcctagt  4560
aatgtcattc tggttctggg tctttttctt tgttgtttta catgtctgtg ttttttttgt  4620
cccgttgatg ttcctgtttt tccctttgg ttctcttttt tcttaagtat ccctgcccct  4680
ggctctctct cttttttttg tgttcgttct cggctcttgt gtctttctct ctgtgtgttt  4740
tttcagcccc ctttctctct gcgaggccgt tctcaggctt ttaaagctag agaaagtcgt  4800
gtgttcatgc cttcagaaat gaggcatgtt ttgtgaggga tcgtgggcat cgtggttcat  4860
gatttgctgg ttgtgtttct tgttgatccg gtcttcaaga tgagaagatg ataaataatg  4920
tacgttgaaa ataacagcga tttcacccga aatgattatt tttaatttgg accctaaact  4980
tctgccattg aacaattagg ttcctgattt cattaattaa acaatttcaa attcaattaa  5040
gtccccaaac ttccaattct tcccatgttt gacataattg atccccaaat ttataattca  5100
atccttatta gtcccatatc aacccaatct ttaattcatt catttttat tttttatata  5160
ttatttttgg ttattacaat ttttattgat tattttcaac ttaaacatga tatgttatgt  5220
tttcagaaac acgcattaaa ctcgctcctg caaatgaaag agacaagcaa cagcttcagt  5280
ggttttgtga tgcatgcaaa ggaataccac aggttcgatt caccccttgta tacagttctt  5340
cttctgtggt catagagcaa atgacaactt gtatgctaca agtagatgag acaatttttc  5400
agctgaagta tttgaatgtg catttttcct ttcctttcat tgaaaccatg ataacatttg  5460
aggacttttt ttttataacg ctataatttc caatgctatc cagattccaa cataactaat  5520
gttagatgct atagccaaat aagaagcctc cttgagaata ggtttgtttt ggagtccagt  5580
agatccattt agaagaggac atgaaaacct ccccttacga acaattctga gccttctaaa  5640
atgggaggaa tgcatgctgt tgtagggaaa tttgttggct ttaatcgttt atttttgggt  5700
tattattggt tttcatgtca ccttgggtca aattgaaaac tcatattgaa gaacaataca  5760
tttgtttcag attgggagaa accaaagctt aaatgtcttt aataaattct aattgttgtc  5820
tcgttgacat gtatttgtat attatgtact ggactacttc ccttgaggtt catagtcccc  5880
cttcaagaat ttatgagccc acagtaaact cttttgaaat gaacactagt cattatgctt  5940
tcctttagac agttatgagt cgcttgctac tatgtaagtg gtagctcatg ctcaaactcc  6000
cctgaaatgc atactagtca ctacgctacg gttattgctg aagaaatgca tttatttctg  6060
attggtgcta ctctacttta ataggtagaa atactctgat cgcaaatcca tacgaactgc  6120
tgattgaggt tcctcttgca cctgattaat tgtttcatat ttaaaattct agcagttgat  6180
ttgcttcctt taaaaaaggt tttttactta aatatgcaga aaaggatcct aatgtcacaa  6240
```

-continued gtgtatctgt ttggttgtga tctgttatag tccaaattct gataagcttt tcaagagtgt 6300
tgcatacctt taaattgaaa ttcccttgtt gtttacatat ctatgtatag agtgggaaat 6360
tttaatgtaa aaacttgcat agtcaataag agctaatatc atttagtcaa agactttgtt 6420
cattacaaga ggacttgtga tacgaatgcc tataatgtta caggtaatgc atcctctaga 6480
atttctgtcc agatctcaga atctggttgt tcaagcaact gctccaccat cggatgaaga 6540
tccagagata gcaatggcag taaatgcctc cattcagtct gccatggcag agcaacctat 6600
ttttgatacc cactctagca ctggagcaag ttcatcctct agctggaatt gccctgttaa 6660
tgatggcggt caaggtgcta tggatgtgcc agcaacacct cctccaaaaa caactagcag 6720
cggatgggca ccttatgaaa gtgtatctag tggcagctca actcagcaaa ccaagatctt 6780
gaatagcagc gttgctgatg tccagacagc aactgatgcc caagattcag tcccatcagc 6840
tccacccatt gtagatgagc ttatagaaga tggtcccatt cactatccat caattgattc 6900
cagcccctt gatttttctt ccctgcccct tgagaattta ccagaaaaca cgggtgaaaa 6960
gaaagaagat ggaggttcat catcatgtgt aatatgttta gatgctccag ttgagggagc 7020
ttgcattcca tgtggccaca tggttggatg tatgtcttgt ttgaaggaaa tcaaagccaa 7080
ggaatggggt tgccctgtgt gtcgtgccac aattaaccag gttgtaaggc tctatgctgt 7140
ttgattcttg ctgaagaatg aaggtataaa tggtaagtat tttctgggca ccatagacaa 7200
ttatgttctc tttcctatag aacagtatat gaccttaact ttcttgtctg aattattaaa 7260
caagtatacc ttagtgtttg tgctttcagt agcatcactg aaatccccta tagtttgaag 7320
ctaatcatcc tccttccgcc gatgtagatc ttacacttgc tacattttgg gaattggaat 7380
tattctctca gtatctaaat cacacaattt aatgctctca aaactgttag gaagtggttg 7440
cattttcatt gggaatagct tgattctagt tttttgggag tctagtgatt tactgtgaga 7500
ctacaaggga gtctcttgat ctccttataa attttaatct aggatcctga tgagagtaaa 7560
atttactaga aacaaaaatg ctaaattgct ggcaaccgtt tctgcaggga agtttggcag 7620
cgcaagagag ttgacaactt gagttgctgc agttgggcaa cttcttggaa cattttactc 7680
gcttacttgt gattagtaat accatgtatg ggttctttaa gggtatgcct tatgtgagcc 7740
ttttgtgtat aatttctttg tatacataag attccaatgt gcttgtatat gaagtcatat 7800
atgaactgcg taaaagggat tcaatgcttt tgcaattttc aaggtaatca tttatgaact 7860
aattctatac ac 7872

SEQ ID NO: 4 moltype = AA length = 507
FEATURE Location/Qualifiers
source 1..507
mol_type = protein
organism = Populus trichocarpa
SEQUENCE: 4
MKFFSIIGNS FGCSASGERL VSAARDGDIQ EAKALLEYNP RLARYSTFGV RNSPLHYSAA 60
QGHHEIVSLL LESGVDINLR NYRGQTALMQ AGQHGHWEVV LTLMLFKANI HRADYLNGGT 120
ALHLAALNGH SRCIRLLLAD YIPSIADCWD ILSKGSRDNG SISEFDGSAL REVINRPADG 180
GITALHMAAL NGHVESVLLL LDLGASAYEV TVEDGTTIDL IGAGSTALHY AACGGNPQCC 240
QILIARGASL TAENAKGWTP LMVARSWHRN ELEVILTTQQ ENQSQICPSP YVSIPFMSIV 300
KIARECGWRN NDSLPTCDDT CVVCLETKCT VAAEGCGHEF CTRCALYLCS TICISTVAQG 360
PTGSVACPLC RHGIVSFVKL PGTKPVVKAI ARTSLSLSFC TCTGEEPDFP SMTTPLRKPD 420
FQCTKISPPS SFRSLSCQKF PSMNFNASRC MGASDTTPLV PCTIDLNPRE REVRCSRSRI 480
RRSTSNPERR KSWLSALNQY VTTGTGC 507

SEQ ID NO: 5 moltype = AA length = 509
FEATURE Location/Qualifiers
source 1..509
mol_type = protein
organism = Populus trichocarpa
SEQUENCE: 5
MKFLSIMGNS LGCSASGERL VSAARDGDIQ EAKALLEYNP RLARYSTFGV RNSPLHYSAA 60
QGHHEIVSLL LESGIDINLR NYRGQTALMQ ACQHGHWEVV LTLMLFKANI HRADYLNGGT 120
ALHLAALNGH SRCIRLLLAD YIPSIADCWE ILSKGSKDNE SISEFDGSAL REVINRPADG 180
GITALHMAAL NGHVESVQLL LDLGASVYEV TVEDGTTIDL IGAGSTALHY AACGGNSQCC 240
QILIARGANL TAENANGWTP SMVACSWHRN ELEEILSSQP GNRSQICPSS YLSIPFMSIV 300
KIARECGWRN NDSLPTCEDA CVVCLERKCT VAAEGCRHEF CTRCALYLCS AICTSTVAQG 360
PTGSVACPLC RHGIVSFVKL PGTKPLVKAI ARTSLSLSFC TCSGEEQDFT SMKTLLCKPD 420
FQCTRISPLS SSFRSLSCRK FPSMNFNASR CMGTSDTSPS LVPCTIDRNL RECLVRCSRS 480
RIRQSTSNTE RRRSWLSALN QYVTTGTGC 509

SEQ ID NO: 6 moltype = AA length = 454
FEATURE Location/Qualifiers
source 1..454
mol_type = protein
organism = Populus trichocarpa
SEQUENCE: 6
MGQGLSCAAS QEHAFFTAVQ LGEFDTVNAM LERDPSLLHQ TTYDRQYPLH IAAANGQIEI 60
LTMLLERSVD PDMVNRHKQT PLMLAAMHGK ISCLKKLIEA GANILKFDSL NGRTCLHYAA 120
YYGHSDCLQA IISAAQSSPV AVSWGYARFV NIRDGRGATP LHLAARQRRP GCVHILLGNG 180
ALVCSSTGGY GSPGSTPLHL AARGGSLDCI RALLAWGADR LQRDASGRIP YVVALKHKNG 240
MCAALLNPSS AEPLVWPSPL KFISELNQEA KALLECALME ANREREKNIL MEANREREKN 300
ILKGSGHSLP SPSHSADGTD YNISEASDTE VCCICFEQVC TIEVQDCGHQ MCAQCTLALC 360
CHNKPNPTTA CLNPPVCPFC RSTIVRLVVA KIKNCNDADQ DIGEIGSPKL RKSRKSRNFS 420
EGSSSFKGLS ATFGKMGGRG SGRIAAENEW MDKP 454

SEQ ID NO: 7 moltype = AA length = 511
FEATURE Location/Qualifiers
source 1..511

-continued

```
                        mol_type = protein
                        organism = Populus trichocarpa
SEQUENCE: 7
MGNSFGCSAS GERLVSAARD GDLVEAKMLL DCNPCLAKYS TFGGLNSPLH FAAAKGHNEI  60
VGLLLENGAD VNSRNYCGQT ALMQACRYGH WEVVQTLLLF RCNVTRADYL NGRTALHFAA  120
VNGHARCIRL VVADFVPSAP FEAMHARIEG DTGDGSSEKN RFDQSALSRF VNKAADGGIT  180
ALHMVALNGY FDCVQLLLDI HANVSSETFH YGTTMDLIGA GSTPLHYAAC GGNLKCCQIL  240
LARGASRTTL NCNGWLPVDV ARMWGRHWLE PLLATNSEST IPRFPHSNYL ALPLLSVLNI  300
ARESGLQCST RSSDDPDICA VCLERACNVA AEGCRHELCV RCALCLCSTC NISSEMVGPT  360
GSIPCPLCRH GIVSFDRLPG SSAKEMKLPL SLGLCAPCML HPRDMDGKSL ACLPEVRKNR  420
VASVSSDFLC PVTCSPFPSV AIPLCTCNDE PCPSLETQEA ESQDESSHRS QTSVEQVKVE  480
GPRLEKTSCS SMFWGRRSCS REHQCTSEIN A                                 511

SEQ ID NO: 8            moltype = AA  length = 511
FEATURE                 Location/Qualifiers
source                  1..511
                        mol_type = protein
                        organism = Populus trichocarpa
SEQUENCE: 8
MGNSFGCSAS GERLVSAARD GDLVEAKMLL DCNPCLAKYS TFGGLNSPLH FAAAKGHNEI  60
VGLLLENGAD VNSRNYCGQT ALMQACRYGH WEVVQTLLLF RCNVIRADYL SGRTALHFAA  120
VNGHVRCIRL VVADFVPSAP FEAMHTQMEG DTRDGSSVKN RFDQSALSRF VNKAADGGIT  180
ALHIAALNGY FDCVQLLLDI HANVSSVTFH YGTTMDLIGA GSTPLHYAAC GGSLKCCQIL  240
LARGASRMTL NCNGWLPVDV ARMWGRHWLE PLLAPNSDSA IPRFPHSNYL SLPLLSVLNI  300
ARESGMHCSV SASDDPDICA VCLERACNVA AEGCGHELCV RCALYLCSTC NIPSEMVGPT  360
GSIPCPLCRH GIVSFVRLPG SSAKEMKLPL SLGLCTPCML HSHDVDGQSP ACLPEVRKNR  420
VVSVSSDFLC PVTCSPFPSV AIPLCTCNDG PCPSFEPQEV ESQDESSHRP QTSVEQDKME  480
GPRLEKTSCS SMFWGRRSCS REHQCNSEIN T                                 511

SEQ ID NO: 9            moltype = AA  length = 442
FEATURE                 Location/Qualifiers
source                  1..442
                        mol_type = protein
                        organism = Populus trichocarpa
SEQUENCE: 9
MGQGLSCAAS QDHRFFSAVH FGDLDTVNAM LERDPSLLYQ TTYDRQYPLH IAAANGQIEI  60
LSMLLERSVD PDMVNRQKQT PLMLAAMHGK ISCVKKLVEA GANMLKFDSL NGRTCLHFAA  120
YYGHSDCLQA ILSAVQSSPV AVSWGYTRFV NIRDGRGATP LHLAARQRRP ECVHILLDNG  180
ALVCSSTGGY GSPGTTPLHL AARGGSLDCI RELLAWGADR MQRDASGRIP YVVALKYRNG  240
TCAALLNPSS AEPLVWPSPL KFISELNQEA KALLECALME ANREREKNIL KGTGYSLPSP  300
SHSDDGTDDN ISEASDTELC CICFEQVCTI EVEDCGHQMC AQCTLALCCH NKPNPTTACL  360
TPPVCPFCRS TIARLVVAKM KDCNDADQDI GDVGSPKLRK SRRSLNFSEG SSSFKGLSAT  420
FGKMGGRGSG RIAAENEWVD KP                                          442

SEQ ID NO: 10           moltype = AA  length = 499
FEATURE                 Location/Qualifiers
source                  1..499
                        mol_type = protein
                        organism = Populus trichocarpa
SEQUENCE: 10
MGQSLDSMTQ KQSKDELLYQ LAIAGNVDAV KALCSEGAIL EWIDRDGKTP LIVACMDSGL  60
YNVAKVLIEM GANVNAYRPG RHAGTPLHHA VKRGLEQTVK LLLSSGANAL VRNDDCQTAL  120
DVARIKGNIN IVRTIESHIC YFTGWLREFY GPGFLRAFAP QFLSRKIWAA VIPQGSSNPM  180
TPKKLELVIY PSSQDVQPRT VIALWNAEIE EPNFNRPDPE LTIFDQSTKT QYKLASANEG  240
DKQQLHWLYD ACSGIPQVML PPMYGNPPTT VPVVGHHTSA EAVGSAMAIG GGSIQSTTED  300
NPLHPNTHQS SEVINANGWE DPVRGDSHNR WGVTVASTHS EARSSGWMGE APKEDHNGCA  360
VPNMGPSGSQ DHVQTRYDIP PVSETSGGNT ASVPSAPSAP PIPDEELDAG PIHYPSFDFS  420
LLDLSVPAIE LGASVTSDVN KGGTSSSCII CWEAPVEGAC IPCGHMAGCM TCLSEIKAKK  480
GVCPICRSNI NQVTRLYAV                                               499

SEQ ID NO: 11           moltype = AA  length = 468
FEATURE                 Location/Qualifiers
source                  1..468
                        mol_type = protein
                        organism = Populus trichocarpa
SEQUENCE: 11
MGQQQSKDEL LYQQVNYGNI GGIKTLCSQG AGLEWIDKEG KTPLILACRN AGTPLHHAAK  60
RGLENTVKLL LSRGANALVT NDDCQTPLQV ARAKGHSIVV RAIESHICLF SGWLREFYGP  120
GFLEVLAPRL VSRDVWVVVL PTGSRNPRRP YKLELAIYSR LQDAQPRTIV ALWKANLEEM  180
KFHHSDPSVM IVDNSTTSRG RRRRRARCRS LNVRQTQIKL APANESDKQQ LQWFCDACKG  240
IQQVMHPPAF LHNSQAPAVQ ATAPPSAEDI EIAMAMNAYI QSAAERPIFD PHSSAGASSS  300
TSWSYPVNTG SQVALETPAA PPPKVTISEL ALHETGATSS STQQTKIQNS SIADVQTATD  360
AQDSVPSAPP IVDEIVEDGP IHYPSIDSSP IDTSSLSVEN LPENTGEKRE DGGSSSCVIC  420
LDALVEGACI PCGHMAGCMS CLKEIKAKKW GCPVCRAKID QVVRLYAV               468
```

REGULATION OF ROOT DEVELOPMENT

CROSS REFERENCE TO RELATED APPLICATION

This application claims the benefit of priority from U.S. Provisional Application No. 63/467,630, filed on May 19, 2023, the entire content of which is incorporated herein by reference.

STATEMENT REGARDING FEDERALLY SPONSORED RESEARCH OR DEVELOPMENT

This disclosure was made with government support under a research project supported by Contract No. DE-AC05-00OR22725 awarded by the U.S. Department of Energy. The government has certain rights in this invention.

INCORPORATION BY REFERENCE OF SEQUENCE LISTING

The Sequence Listing in an XML format, named as 42947_4872_2_SequenceListing of 24 KB, created on May 15, 2024, and submitted to the United States Patent and Trademark Office via Patent Center, is incorporated herein by reference.

BACKGROUND

Adventitious root (AR) formation and development have been recognized as one of the most important traits in woody species breeding programs (Miller, A. J. et al., *Am J Bot,* 98, 1389-414, 2011). Successful rooting is a prerequisite for the survival of clonally propagated woody species, such as *Populus* (Bannoud, F. et al., *Frontiers in Plant Science,* 12, 2021). In many clonally propagated species, AR formation starts from the dedifferentiation of a specified cell type, followed by the formation of root meristem and AR primordia resulting in the emergence of Ars (Bellini, C. et al., *Annu Rev Plant Biol,* 65, 639-66, 2014; Díaz-Sala, C., *Plants,* 9, 1789, 2020). These processes are tightly regulated by endogenous hormone signals and external nutrient status (Lakehal, A. et al., *Physiologia Plantarum,* 165, 90-100, 2019; De Almeida, M. R. et al., *Trees,* 31, 1377-1390, 2017). Although different approaches have been employed to identify genes involved in AR formation across multiple plant species, the number of functionally characterized regulators is limited (Li, S. W., *Front Plant Sci,* 12, 614072, 2021; Sun, P. et al., *Int J Mol Sci,* 20, 2019; Trupiano, D. et al., *Planta,* 238, 271-282, 2013). As such, identifying genetic engineering and breeding targets that can be used to improve these traits remains a critical pursuit.

SUMMARY OF THE DISCLOSURE

Clonal propagation is a commonly utilized technique in horticulture, agriculture, and forestry because it is an economically efficient method. The formation and growth of adventitious roots are essential for the success of clonal propagation for perennial tree species (Díaz-Sala, C., *Plants,* 9, 1789, 2020). *Populus* is a model perennial woody species with extensive genomic and genetic resources (Tuskan et al., *Science,* 313, 1596-1604, 2006; Muchero et al., *Proceedings of the National Academy of Sciences, USA,* 115, 11573-11578, 2018). Taking advantage of *Populus* natural variation and transcriptomics data, the present disclosure identifies genetic determinants of plant growth and development and elucidate the underlying transcriptional regulatory networks using eQTL (expression quantitative trait loci) methods. The present disclosure identifies XB3 family protein 8 in *Populus trichocarpa* (PtrXB38), as a key hub gene of root development and plant hormone signaling in *Populus*. The present disclosure demonstrates that PtrXB38 regulates both stem-born and base-born adventitious root formation. Omics studies reveals that endogenous plant hormones especially auxin signaling play crucial roles in PtrXB38-mediated adventitious root formation. This disclosure provides a method to genetically engineer plants by manipulating the expression of PtrXB38 polypeptide to increase root development.

One aspect of the present disclosure is directed to a genetically modified plant, plant cell or plant tissue, comprising an exogenous nucleic acid which comprises a nucleotide sequence encoding a PtrXB38 polypeptide or a homolog thereof, wherein the genetically modified plant, plant cell or plant tissue displays an enhanced expression of the PtrXB38 polypeptide or the homolog thereof and an increase in root development compared to a wild-type plant, plant cell, or plant tissue.

In some embodiments, the nucleotide sequence has at least 90% sequence identity to the nucleotide sequence shown in SEQ ID NO: 1. In some embodiments, the PtrXB38 polypeptide or the homolog thereof has at least 90% sequence identity to the amino acid sequence shown in SEQ ID NO: 2.

In some embodiments, the exogenous nucleic acid is stably integrated into the plant genome. In some embodiments, the nucleotide sequence is operably linked to a heterologous promoter.

In some embodiments, the heterologous promoter is a constitutive promoter, an inducible promoter, or a native promoter. In some embodiments, the heterologous promoter is a 35S promoter.

In some embodiments, the plant is a monocot or a dicot.

In some embodiments, the plant is selected from the group consisting of genera *Acer, Afzelia, Allium, Arabidopsis, Agrostis, Avena, Betula, Brassica, Capsicum, Citrullus, Cucumis, Eucalyptus, Fagus, Festuca, Fraxinus, Fragaria, Glycine, Gossypium, Hordeum, Ipomoea, Jatropha, Juglans, Lemna, Lolium, Malus, Manihot, Medicago, Micropus, Milium, Miscanthus, Nicotiana, Oryza, Pennisetum, Phalaris, Phleum, Picea, Pinus, Poa, Populus, Prunus, Quercus, Rosa, Salix, Solanum, Sorghum, Spinacia, Tectona, Trifolium, Triticum, Panicum, Saccharum, Setaria, Zea*, and *Zoysia.*

In some embodiments, the plant is *Populus*. In some embodiments, the plant is *Populus trichocarpa.*

In some embodiments, the root development comprises adventitious root formation.

In some embodiments, the adventitious root formation requires auxin transport and signaling. In some embodiments, the adventitious root formation requires ethylene biosynthesis and signaling.

In some embodiments, the enhanced expression of the PtrXB38 polypeptide or the homolog thereof increases flavonoids in roots, thereby increasing the resilience of the plant roots to environmental stresses.

In some embodiments, the plant displays one or more of the following characteristics:

has improved plant defense against pathogens by increasing production of ethylene and jasmonates compared to a wild type plant;

has increased flooding tolerance compared to a wild type plant; and has increased carbon dioxide ($CO_2$) absorption or carbon dioxide ($CO_2$) sequestration compared to a wild type plant.

Another aspect of the disclosure is directed to a method of increasing root development in a plant, plant cell or plant tissue, comprising introducing into the plant, plant cell or plant tissue, an exogenous nucleic acid sequence encoding a PtrXB38 polypeptide or a homolog thereof, thereby obtaining a genetically modified plant, plant cell or plant tissue, wherein the genetically modified plant, plant cell or plant tissue displays an enhanced expression of the PtrXB38 polypeptide or the homolog thereof and an increase in root development compared to a wild-type plant, plant cell, or plant tissue.

Another aspect of this disclosure is directed to a method of improving plant defense against pathogens in a plant, plant cell or plant tissue comprising enhancing expression of a PtrXB38 polypeptide or a homolog thereof in the plant, plant cell or plant tissue, thereby increasing production of ethylene and jasmonates compared to a wild type plant.

Another aspect of this disclosure is directed to a method of increasing flooding tolerance in a plant, plant cell or plant tissue comprising enhancing expression of a PtrXB38 polypeptide or a homolog thereof in the plant, plant cell or plant tissue, thereby increasing root development compared to a wild type plant.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIGS. 3A-3D. Auxin signaling and transport is essential for PtrXB38-mediated adventitious root formation. (A) Log-fold changes of transcript levels of auxin biosynthesis, signaling, transport and response related genes in 12-day-old root samples of PtrXB38-OE versus control plants, based on RNA-seq results. (B) Log-fold changes of protein abundance of auxin response factor in 12-day-old root samples of PtrXB38-OE versus control plants, based on quantitative proteomics. (C) Root formation of PtrXB38-OE plants upon auxin transport inhibitor treatment. (D) Adventitious root number of PtrXB38-OE plants with 0.2 μM and 1 μM NPA treatments. Bar charts represent mean±s.e.m, and different letters represent significant difference between groups ($P \leq 0.05$) determined by one-way ANOVA followed by Tukey's test.

FIGS. 4A-4F. PtrXB38-regulated adventitious root development involves ethylene biosynthesis and signaling. (A) Log-fold changes of transcript levels of ethylene biosynthesis genes in 12-day-old root samples of PtrXB38-OE versus control plants, based on RNA-seq. (B) Log-fold changes of protein abundance of ethylene biosynthesis enzymes in 12-day-old root samples of PtrXB38-OE versus control plants, based on quantitative proteomics. (C) Root formation of PtrXB38-OE plants upon ethylene biosynthesis inhibitor AVG treatment at 5 μM. (D) Log-fold changes of transcription levels of ERF genes in 12-day-old root samples of PtrXB38-OE versus control plants, based on RNA-seq. (E) Root morphology of PtrXB38-OE plants upon AVG treatment at 1 μM. (F) Root biomass of PtrXB38-OE in (E). Bar charts represent mean±s.e.m, and different letters represent significant difference between groups ($P \leq 0.05$) determined by one-way ANOVA followed by Tukey's test.

FIGS. 5A-5J. PtrXB38 affects flavan-3-ols biosynthesis in poplar. (A) Changes in root color of PtrXB38-OE plants. (B) Anthocyanin accumulation in the roots of PtrXB38-OE plants. (C) Schematic diagram of phenylpropanoid pathway and flavonoid biosynthesis. (D-H) Metabolite abundance of shikimic acid (D), phenylalanine (E), catechin (F), epicatechin (G), and epigallocatechin (H) in PtrXB38-OE plants. (I) Log-fold changes of transcript levels of phenylpropanoid pathway and flavonoid biosynthetic genes in leaf samples of PtrXB38-OE plants. Data is retrieved from RNA-seq results. (J) Log-fold changes of protein abundance of phenylpropanoid pathway and flavonoid biosynthetic genes in leaf samples of PtrXB38-OE plants. Data is retrieved from quantitative proteomics results. Bar charts represent mean±s.e.m, and different letters represent significant difference between groups ($P \leq 0.05$) determined by one-way ANOVA followed by Tukey's test.

DETAILED DESCRIPTION

Definitions

Figures 1A, 1B, 1C:
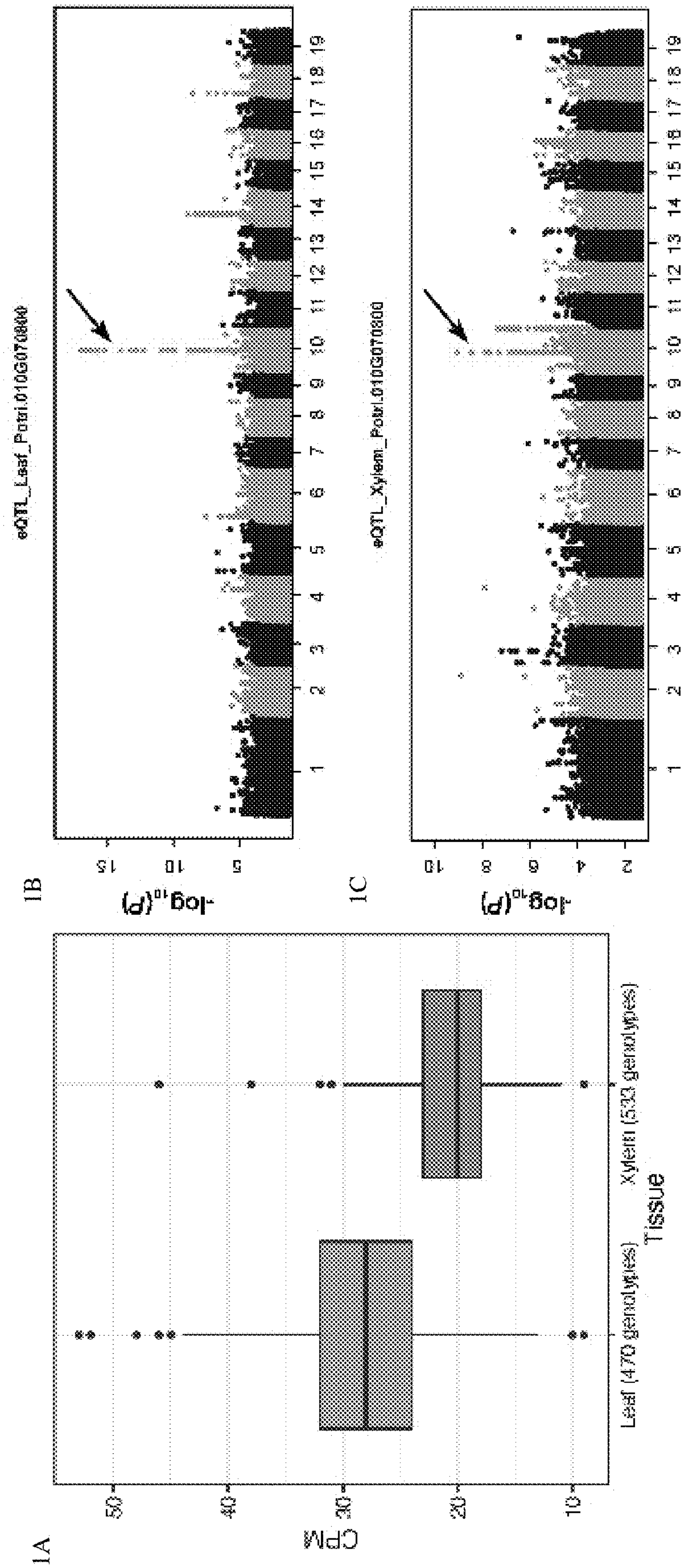
FIGS. 1A-1T. Identification of PtrXB38 as a hotspot by eQTL mapping. (A) Leaf and xylem expression of PtrXB38 across *P. trichocarpa* population. (B-E) Manhattan plots and quantile-quantile plots showing the identification of PtrXB38 as a cis-eQTL hotspot in leaf (B, D) and xylem (C, E). Displayed are −log 10 (P values) for association by genomic position. Chromosome (Chr) 10 containing the associated single nucleotide polymorphisms (SNPs) in PtrXB38 locus is highlighted in green. Chromosomal location of PtrXB38 is marked with arrows. (F, G) Association of the expression of PtrXB38 with one of the SNPs at the PtrXB38 locus, Chr10:9762348, from leaf (F) or xylem (G) transcriptome data. Genotype 0_1 is heterozygous of reference and alternative, and genotype 1_1 is the homozygous alternative. (H-O) Manhattan plots and quantile-quantile plots showing association of the expression of SCZ, OBP4, TCP20 and SVP by genomic position. Chr10 containing the associated SNPs in PtrXB38 locus is highlighted in green. Chromosomal location of PtrXB38 is marked with arrows. (P-S) Association of the expression of SCZ (P), OBP4 (Q), TCP20 (R), and SVP (S) with one of the SNPs at the PtrXB38 locus, Chr10:9762348. Genotype 01 is heterozygous of reference and alternative, and genotype 11 is the homozygous alternative. (T) The TF-based PtrXB38 regulatory network from eQTL network. The expression profiles of the second layer of TFs were used as phenotypes in the eQTL analysis and the highly associated SNPs flanking genes were extracted as the first layer of regulatory genes. The brown nodes represent the first layer of TFs, and the blue nodes represent the second layer of TFs. The green and orange edges represent the eQTL regulatory relationship was obtained from leaf and xylem dataset, respectively.
Figures 1D, 1E, 1F, 1G:
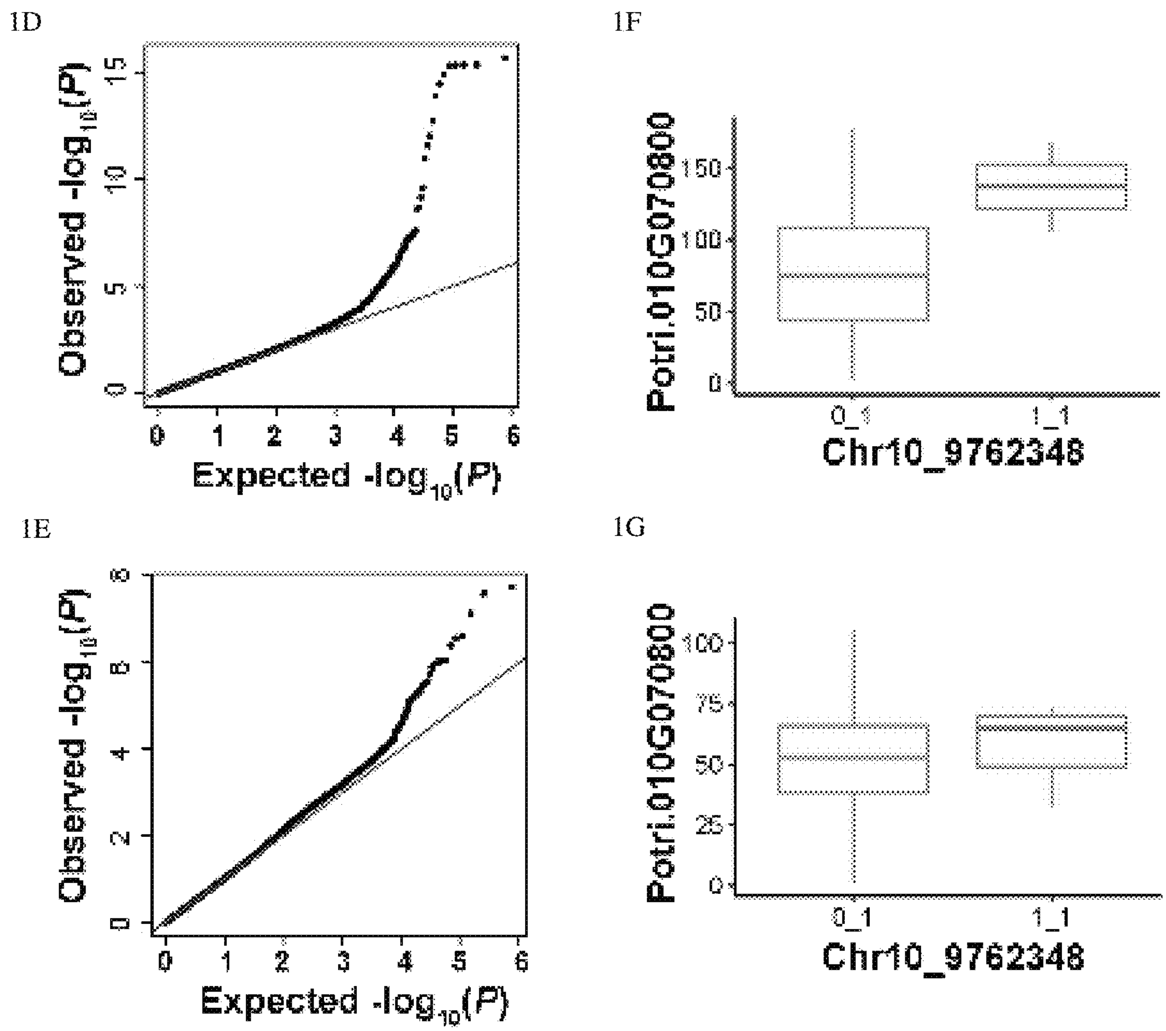
Figures 1H, 1I, 1J, 1K:
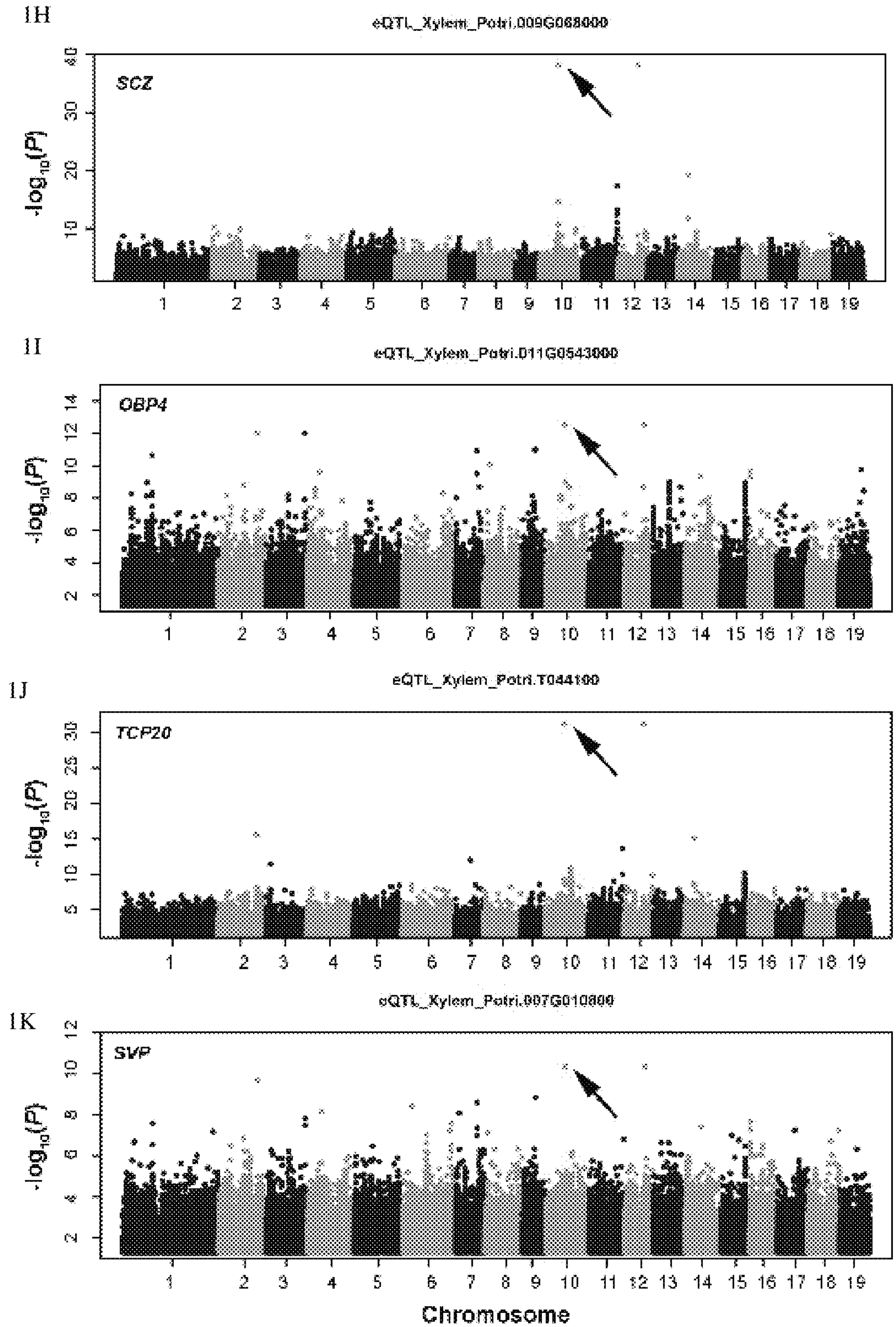
Figures 1L, 1M, 1N, 1O, 1P, 1Q, 1R, 1S:
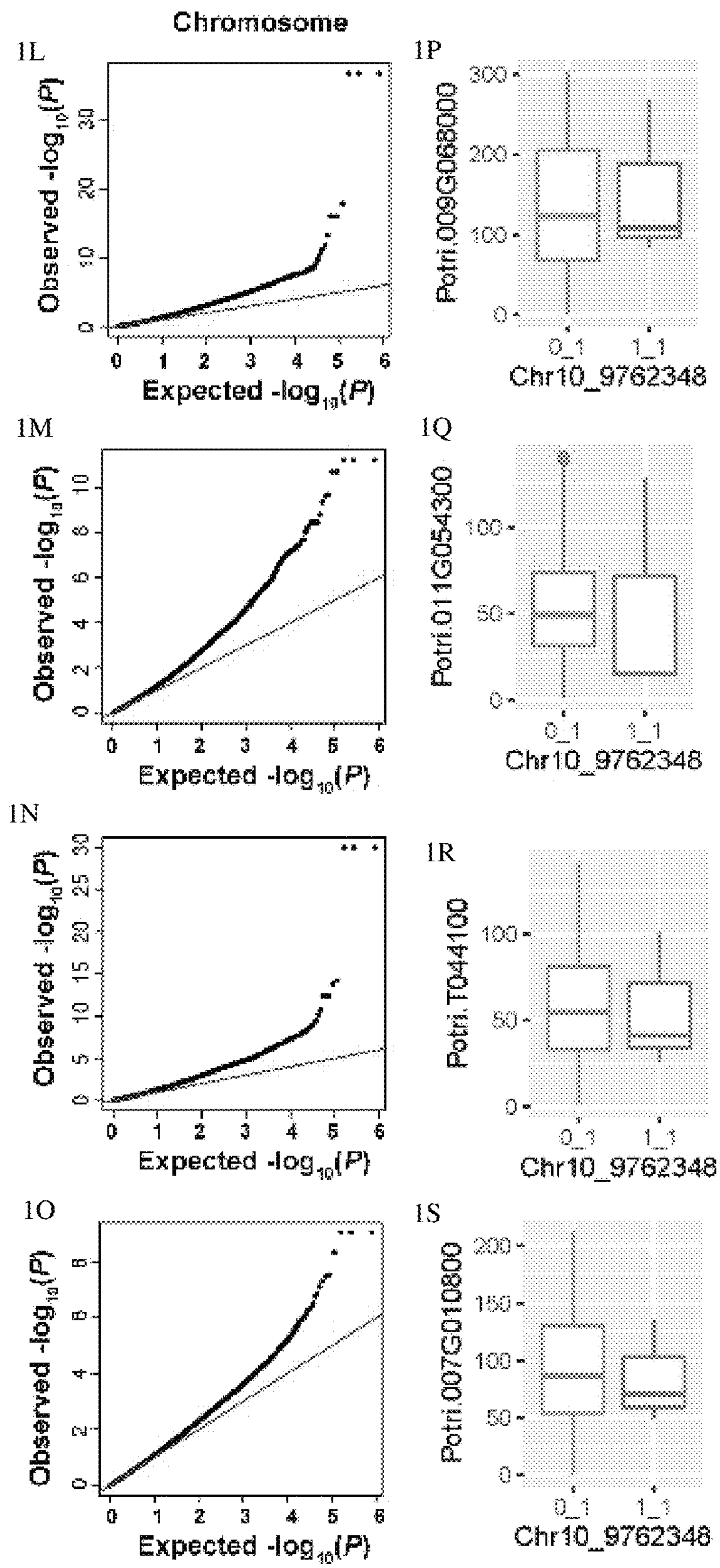

Unless defined otherwise, all technical and scientific terms used herein have the same meaning as commonly understood by one of ordinary skill in the art to which this invention belongs.

As used herein, the term "about" refers to an approximately +/−10% variation from a given value.

The term "control plant" as used herein, refers to a plant of the same species that does not comprise the modification or modifications described in this disclosure. In some embodiments, the control plant is of the same variety. In some embodiments, the control plant is of the same genetic background. In some embodiments, the control plant is wild-type plant.

The term "adventitious root (AR) formation" as used herein, refers to a postembryonic organogenesis process induced by differentiated cells other than those specified to develop roots. Adventitious root formation is a key step in vegetative propagation by stem cuttings, and has been exploited in horticulture, agriculture, and forestry. Lateral and adventitious roots arise by cell divisions in localized areas in the pericycle in the root and vascular parenchyma cells in stem or leaf tissues. Adventitious roots, arising from the stem of the plants, are the main component of the mature root system of many plants. Their development can also be induced in response to adverse environmental conditions or stresses. Auxin is the major growth-promoting hormone for the initiation of lateral and adventitious root growth. It induces cells in the pericycle and parenchyma to dedifferentiate and enter initial cell divisions.

As used herein, the term "auxin response factors (ARFs)" refers to a family of transcription factors that play an important role of auxin regulation through their binding with auxin response elements.

As used herein, the term "ethylene response factors (ERFs)" refers to AP2/ERF superfamily proteins belonging to the largest family of transcription factors known to participate during multiple abiotic stress tolerance such as salt, drought, heat, and cold with well-conserved DNA-binding domain.

The term "exogenous" as used herein, refers to a substance or molecule originating or produced outside of an organism. The term "exogenous gene" or "exogenous nucleic acid molecule" as used herein, refers to a nucleic acid that codes for the expression of an RNA and/or protein that has been introduced ("transformed") into a cell or a progenitor of the cell. An exogenous gene may be from a different species (and so a "heterologous" gene) or from the same species (and so a "homologous" gene), relative to the cell being transformed. A transformed cell may be referred to as a recombinant or genetically modified cell. An "endogenous" nucleic acid molecule, gene, or protein can represent the organism's own gene or protein as it is naturally produced by the organism.

The term "expression" refers to the process of converting genetic information of a polynucleotide into RNA through transcription, which is catalyzed by an enzyme, RNA polymerase and into protein, through translation of mRNA on ribosomes. Expression can be, for example, constitutive or regulated, such as, by an inducible promoter (e.g., lac operon, which can be triggered by Isopropyl β-D-1-thiogalactopyranoside (IPTG). Up-regulation or overexpression refers to regulation that increases the production of expression products (mRNA, polypeptide or both) relative to basal or native states, while inhibition or down-regulation refers to regulation that decreases production of expression products (mRNA, polypeptide or both) relative to basal or native states. Expression of a gene can be measured through a suitable assay, such as real-time quantitative reverse transcription polymerase chain reaction (qRT-PCR), Northern blot, transcriptome sequencing and Western blot.

The term "gene" as used herein, refers to a segment of nucleic acid that encodes an individual protein or RNA and can include both exons and introns together with associated regulatory regions such as promoters, operators, terminators, 5' untranslated regions, 3' untranslated regions, and the like.

The term "genetically modified" (or "genetically engineered" or "transgenic" or "cisgenic") refers to a plant comprising a manipulated genome or nucleic acids. In some embodiments, the manipulation is the addition of exogenous nucleic acids to the plant. In some embodiments, the manipulation is changing the endogenous genes of the plant.

The term "homologous" refers to nucleic acids or polypeptides that are highly related at the level of nucleotide or amino acid sequence. Nucleic acids or polypeptides that are homologous to each other are termed "homologues". The term "homolog" refers to a gene related to a second gene by descent from a common ancestral DNA sequence, therefore, the corresponding polynucleotide/polypeptide has a certain degree of homology, i.e., sequence identity (at least 10%, at least 20%, at least 40%, at least 60%, 65%, 66%, 68%, 70%, 75%, 80%, 86%, 88%, 90%, 92%, 95%, 97% or 99%). A "homolog" furthermore means that the function is equivalent to the function of the original gene.

Homologs of a given gene and corresponding or equivalent positions in the homologous genes or proteins can be determined by sequence alignment programs, e.g., including but not limited to, NCBI BLAST, ClustalW, DIAMOND, CS-BLAST, and MAFFT.

As used herein, the term "nucleic acid" has its general meaning in the art and refers to a coding or non-coding nucleic sequence. Nucleic acids include DNA (deoxyribonucleic acid) and RNA (ribonucleic acid) nucleic acids. Examples of nucleic acid thus include but are not limited to DNA, mRNA, tRNA, rRNA, tmRNA, miRNA, piRNA, snoRNA, and snRNA. Nucleic acids thus encompass coding and non-coding region of a genome (i.e., nuclear or mitochondrial or chloroplast).

The term "operably linked" refers to positioning of a regulatory region and a sequence to be transcribed in a nucleic acid so as to influence transcription or translation of such a sequence. For example, to bring a coding sequence under the control of a regulatory region, the translation initiation site of the translational reading frame of the polypeptide is typically positioned between one and about fifty nucleotides downstream of the promoter. A regulatory region can, however, be positioned as much as about 5,000 nucleotides upstream of the translation initiation site or about 2,000 nucleotides upstream of the transcription start site. A regulatory region typically comprises at least a core (basal) promoter.

The term "regulatory region" refers to a nucleic acid having nucleotide sequences that influence transcription or translation initiation and rate and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns and combinations thereof.

A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene (Fromm et al., *The Plant Cell,* 1:977-984 (1989)). The choice of regulatory regions to be included depends upon several factors, including, but not limited to, efficiency, selectability, inducibility, desired expression level and cell- or tissue-preferential expression. It is a routine matter for one of skill in the art to modulate the expression of a coding sequence by appropriately selecting and positioning regulatory regions relative to the coding sequence.

A "vector" is a replicon, such as a plasmid, phage or cosmid, into which another DNA segment may be inserted so as to bring about the replication of the inserted segment. Generally, a vector is capable of replication when associated with the proper control elements. Suitable vector backbones include, for example, those routinely used in the art such as plasmids, viruses, artificial chromosomes, BACs, YACs or PACs. The term "vector" includes cloning and expression vectors, as well as viral vectors and integrating vectors. An "expression vector" is a vector that includes a regulatory region. Suitable expression vectors include, without limitation, plasmids and viral vectors derived from, for example, bacteriophage, baculoviruses and retroviruses. Numerous vectors and expression systems are commercially available from such corporations as Novagen (Madison, Wis.), Clontech (Mountain View, Calif.), Stratagene (La Jolla, Calif.) and Invitrogen/Life Technologies (Carlsbad, Calif.).

PtrXB38 is also referred to as PtrXBAT35. PtrXB38 polypeptide is also referred to as PtrXBAT35 polypeptide. XB gene family is also referred to as XBAT gene family.

Plants

There is no specific limitation on the plants that can be used in the methods of the present disclosure, as long as the plant is suitable to be transformed by a gene. The term "plant" as used herein, includes whole plants, plant tissues or plant cells. The plants that can be used for the methods and compositions of the present disclosure include various crops, flower plants or plants of forestry, etc. Specifically, the plants include, but are not limited to, dicotyledon, monocotyledon or gymnosperm.

In some embodiments, the methods and compositions of the present disclosure are also applicable over a broad range of plant species from the dicot genera *Acer, Afzelia, Arabidopsis, Betula, Brassica, Eucalyptus, Fagus, Fraxinus, Glycine, Gossypium, Jatropha, Juglans, Linum, Lycopersicon, Medicago, Micropus, Populus, Prunus, Quercus, Salix, Solanum, Tectona* and *Trifolium*; and the monocot genera *Agrostis, Avena, Festuca, Hordeum, Lemna, Lolium, Milium, Miscanthus, Oryza, Panicum, Pennisetum, Phalaris, Phleum, Poa, Saccharum, Secale, Sorghum, Triticum, Zea* and *Zoysia*; and the gymnosperm genera *Abies, Picea* and *Pinus*. In certain embodiments, the polynucleotides and vectors described herein can be used to transform a number of monocotyledonous and dicotyledonous plants and plant cell systems, wherein such plants are hybrids of different species.

Expression Vectors

The polynucleotides and expression vectors described herein can be used to increase the expression of a PtrXB38 polypeptide or the homolog thereof in plants, plant cells or plant tissues.

The vectors provided herein can include origins of replication, scaffold attachment regions (SARs) and/or marker genes. A marker gene can confer a selectable phenotype on a plant cell. For example, a marker can confer biocide resistance, such as resistance to an antibiotic (e.g., kanamycin, G418, bleomycin or hygromycin) or an herbicide (e.g., chlorosulfuron or phosphinothricin). In addition, an expression vector can include a tag sequence designed to facilitate manipulation or detection (e.g., purification or localization) of the expressed polypeptide. Tag sequences, such as green fluorescent protein (GFP), glutathione S-transferase (GST), polyhistidine, c-myc, hemagglutinin or Flag-tag (Kodak, New Haven, Conn.) sequences can be expressed as a fusion with the encoded polypeptide.

Such tags can be inserted anywhere within the polypeptide, including at either the carboxyl or amino terminus. As described herein, plant cells can be transformed with a recombinant nucleic acid construct to express a polypeptide of interest.

Promoters

A variety of promoters are available for use, depending on the degree of expression desired. For example, a broadly expressing promoter promotes transcription in many, but not necessarily all, plant tissues. Non-limiting examples of broadly expressing promoters that can be included in the nucleic acid constructs provided herein include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter and ubiquitin promoters such as the maize ubiquitin-1 promoter.

In some embodiments, the promoter to drive expression of genes of interest is a constitutive promoter. In some embodiments the constitutive promoter is selected from the group consisting of a ubiquitin promoter, a cauliflower mosaic virus (CaMV) 35S promoter, an actin promoter, a peanut chlorotic streak caulimovirus promoter, a *Chlorella* virus methyltransferase gene promoter, a full-length transcript promoter form figwort mosaic virus, a pEMU promoter, a MAS promoter, a maize H3 histone promoter and an *Agrobacterium* gene promoter.

In some embodiments, the promoter to drive expression of genes of interest is a regulated promoter. In some embodiments the regulated promoter is selected from the group consisting of a stress induced promoter, chemical-induced promoter, a light induced promoter, a dark-induced promoter, and a circadian-clock controlled promoter.

Some suitable regulatory regions initiate transcription, only or predominantly, in certain cell types. For instance, promoters active in photosynthetic tissue confer transcription in green tissues such as leaves and stems. Examples of such promoters include the ribulose-1,5-bisphosphate carboxylase (RbcS) promoters such as the RbcS promoter from eastern larch (*Larix laricina*), the pine chlorophyll a/b binding-6 (cab6) promoter (Yamamoto et al., 1994, *Plant Cell Physiol.,* 35:773-778), the chlorophyll a/b binding-1 (Cab-1) promoter from wheat (Fejes et al., 1990, *Plant Mol. Biol.,* 15:921-932), the chlorophyll a/b binding-1 (CAB-1) promoter from spinach (Lubberstedt et al., 1994, *Plant Physiol.,* 104:997-1006), the cab IR promoter from rice (Luan et al., 1992, *Plant Cell,* 4:971-981), the pyruvate orthophosphate dikinase (PPDK) promoter from corn (Matsuoka et al., 1993. *Proc. Natl. Acad. Sci. USA,* 90:9586-9590), the tobacco light-harvesting complex of photosystem (Lhcb1*2) promoter (Cerdan et al., 1997, *Plant Mol. Biol.,* 33:245-), the *Arabidopsis* SUC2 sucrose-H+ symporter promoter (Truernit et al., 1995, *Planta,* 196:564-570) and thylakoid membrane protein promoters from spinach (psaD, psaF, psaE, PC, FNR, atpC, atpD, cab, rbcS).

In some embodiments, promoters of the instant application comprise inducible promoters. Inducible promoters confer transcription in response to external stimuli such as chemical agents or environmental stimuli. For example, inducible promoters can confer transcription in response to hormones such as gibberellic acid or ethylene or in response to light, nitrogen, shade or drought.

A basal promoter is the minimal sequence necessary for assembly of a transcription complex required for transcription initiation. Basal promoters frequently include a “TATA box” element that may be located between about 15 and about 35 nucleotides upstream from the site of transcription initiation. Basal promoters also may include a “CCAAT box” element (typically the sequence CCAAT) and/or a GGGCG sequence, which can be located between about 40 and about 200 nucleotides, typically about 60 to about 120 nucleotides, upstream from the transcription start site.

A 5' untranslated region (UTR) can be included in nucleic acid constructs described herein. A 5' UTR is transcribed but is not translated and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

It will be understood that more than one regulatory region may be present in a vector, e.g., introns, enhancers, upstream activation regions, transcription terminators and inducible elements. Regulatory regions, such as promoters for endogenous genes, can be obtained by chemical synthesis or by subcloning from a genomic DNA that includes such a regulatory region. A nucleic acid comprising such a regulatory region can also include flanking sequences that contain restriction enzyme sites that facilitate subsequent manipulation.

Techniques for introducing nucleic acids into monocotyledonous and dicotyledonous plants, plant cells or plant tissues are known in the art and include, without limitation, *Agrobacterium*-mediated transformation, viral vector-mediated transformation, electroporation and particle gun transformation, e.g., U.S. Pat. Nos. 5,538,880, 5,204,253, 6,329,571 and 6,013,863, incorporated herein by reference in their entirety. If a cell or tissue culture is used as the recipient tissue for transformation, plants can be regenerated from transformed cultures if desired, by techniques known to those skilled in the art. See, e.g., Niu et al., 2000. *Plant Cell* Rep. V19:304-310; Chang and Yang, 1996, *Bot. Bull. Acad. Sin*., V37:35-40; and Han et al., 1999, *Biotechnology in Agriculture and Forestry*, V44:291 (ed. by Y. P. S. Bajaj), Springer-Vernag.

Disclosed herein are plants, plant cells and plant tissues genetically modified by introduction of an exogenous nucleic acid, e.g., provided in an expression vector, thereby resulting in genetically modified plants, plant cells and plant tissues that display increased root development.

Typically, genetically modified plant cells used in methods described herein constitute part or all of a whole plant. Such plants can be grown in a manner suitable for the species under consideration, either in a growth chamber, a greenhouse or in a field. Genetically modified plants can be bred as desired for a particular purpose, e.g., to introduce a recombinant nucleic acid into other lines, to transfer a recombinant nucleic acid to other species or for further selection of other desirable traits. Progeny includes descendants of a particular plant or plant line provided the progeny inherits the transgene. Progeny of a plant include seeds formed on F1, F2, F3, F4, F5, F6 and subsequent generation plants or seeds formed on BC1, BC2, BC3 and subsequent generation plants or seeds formed on F1BC1, F1BC2, F1BC3 and subsequent generation plants. Seeds produced by a genetically modified plant can be grown and then selfed (or outcrossed and selfed) to obtain seeds homozygous for the nucleic acid construct. Alternatively, genetically modified plants can be propagated vegetatively for those species amenable to such techniques.

In some embodiments, the genetically modified plant, plant cell, or plant tissue, comprises an exogenous nucleic acid which comprises a nucleotide sequence encoding a PtrXB38 polypeptide or a homolog thereof, wherein the genetically modified plant, plant cell or plant tissue displays an enhanced expression of the PtrXB38 polypeptide or the homolog thereof and an increase in root development compared to a wild-type plant, plant cell, or plant tissue.

By "increased expression" it means the expression of the PtrXB38 polypeptide or the homolog thereof is increased as compared to a control plant, plant cell or plant tissue (e.g., a wild type plant, plant cell or plant tissue without the genetic modification, or a plant cell or plant tissue introduced with a control vector without the nucleotide sequence encoding the PtrXB38 polypeptide or the homolog thereof). The expression of the PtrXB38 polypeptide or the homolog thereof can be measured based on the gene expression (e.g., mRNA level) or the protein production (protein level). The extent of increase can be at least 50%, 100% (2 fold), 3 fold, 4 fold, 5 fold, 10 fold, 15 fold, or greater. In some embodiments, the increase is at least 2 fold. In some embodiments, the increase is at least 5 fold. In some embodiments, the increase is at least 10 fold.

In some embodiments, the root development comprises adventitious root formation. By "increase in root development", it can include increase in root numbers and/or increase in root length from a genetically modified plant, plant cell or plant tissue, as compared to a control plant, plant cell or plant tissue without the genetic modification. The extent of increase, e.g., in the number of roots, can be at least 20%, 30%, 40%, 50%, 100% (2 fold), 3 fold, 4 fold, 5 fold, 10 fold, 15 fold, or greater. In some embodiments, the increase is at least 2 fold. In some embodiments, the increase is at least 5 fold. In some embodiments, the increase is at least 10 fold.

In some embodiments, the nucleotide sequence encoding a PtrXB38 polypeptide or a homolog thereof is set forth in SEQ ID NO: 1. In some embodiments, the nucleotide sequence has at least 90% sequence identity to the nucleotide sequence shown in SEQ ID NO: 1. In some embodiments, the nucleotide sequence has at least 91% sequence identity to the nucleotide sequence shown in SEQ ID NO: 1. In some embodiments, the nucleotide sequence has at least 92% sequence identity to the nucleotide sequence shown in SEQ ID NO: 1. In some embodiments, the nucleotide sequence has at least 93% sequence identity to the nucleotide sequence shown in SEQ ID NO: 1. In some embodiments, the nucleotide sequence has at least 94% sequence identity to the nucleotide sequence shown in SEQ ID NO: 1. In some embodiments, the nucleotide sequence has at least 95% sequence identity to the nucleotide sequence shown in SEQ ID NO: 1. In some embodiments, the nucleotide sequence has at least 96% sequence identity to the nucleotide sequence shown in SEQ ID NO: 1. In some embodiments, the nucleotide sequence has at least 97% sequence identity to the nucleotide sequence shown in SEQ ID NO: 1. In some embodiments, the nucleotide sequence has at least 98% sequence identity to the nucleotide sequence shown in SEQ ID NO: 1. In some embodiments, the nucleotide sequence has at least 99% sequence identity to the nucleotide sequence shown in SEQ ID NO: 1.

In some embodiments, the nucleotide sequence encoding a PtrXB38 polypeptide or a homolog thereof is a genomic DNA sequence set forth as in SEQ ID NO: 3.

In some embodiments, the PtrXB38 polypeptide or the homolog thereof has an amino acid sequence as laid out in SEQ ID NO: 2. In some embodiments, the PtrXB38 polypeptide or the homolog thereof has at least 90% sequence identity to the amino acid sequence shown in SEQ ID NO: 2. In some embodiments, the PtrXB38 polypeptide or the homolog thereof has at least 91% sequence identity to the amino acid sequence shown in SEQ ID NO: 2. In some embodiments, the PtrXB38 polypeptide or the homolog thereof has at least 92% sequence identity to the amino acid sequence shown in SEQ ID NO: 2. In some embodiments, the PtrXB38 polypeptide or the homolog thereof has at least 93% sequence identity to the amino acid sequence shown in SEQ ID NO: 2. In some embodiments, the PtrXB38 polypeptide or the homolog thereof has at least 94% sequence identity to the amino acid sequence shown in SEQ ID NO: 2. In some embodiments, the PtrXB38 polypeptide or the homolog thereof has at least 95% sequence identity to the amino acid sequence shown in SEQ ID NO: 2. In some embodiments, the PtrXB38 polypeptide or the homolog thereof has at least 96% sequence identity to the amino acid sequence shown in SEQ ID NO: 2. In some embodiments, the PtrXB38 polypeptide or the homolog thereof has at least 97% sequence identity to the amino acid sequence shown in SEQ ID NO: 2. In some embodiments, the PtrXB38 polypeptide or the homolog thereof has at least 98% sequence identity to the amino acid sequence shown in SEQ ID NO: 2. In some embodiments, the PtrXB38 polypeptide or the homolog thereof has at least 99% sequence identity to the amino acid sequence shown in SEQ ID NO: 2.

PtrXB38 belongs to a nine-member protein family. In some embodiments, the homologs of PtrXB38 include the other eight members: PtrXB31, PtrXB32, PtrXB33, PtrXB34, PtrXB35, PtrXB36, PtrXB37 and PtrXB39. These homologs share same protein domains (ANK domain and RING domain). In some embodiments, the PtrXB31 polypeptide has an amino acid sequence as laid out in SEQ ID NO: 4 which has 13.73% sequence identity to the amino acid sequence shown in SEQ ID NO: 2. In some embodiments, the PtrXB32 polypeptide has an amino acid sequence as laid out in SEQ ID NO: 5 which has 13.40% sequence identity to the amino acid sequence shown in SEQ ID NO: 2. In some embodiments, the PtrXB32 polypeptide is excluded from the homologs of PtrXB38 for purposes of this disclosure. In some embodiments, the PtrXB33 polypeptide has an amino acid sequence as laid out in SEQ ID NO: 6 which has 14.78% sequence identity to the amino acid sequence shown in SEQ ID NO: 2. In some embodiments, the PtrXB34 polypeptide has an amino acid sequence as laid out in SEQ ID NO: 7, which has 15.38% sequence identity to the amino acid sequence shown in SEQ ID NO: 2. In some embodiments, the PtrXB35 polypeptide has an amino acid sequence as laid out in SEQ ID NO: 8 which has 15.47% sequence identity to the amino acid sequence shown in SEQ ID NO: 2. In some embodiments, the PtrXB36 polypeptide has an amino acid sequence as laid out in SEQ ID NO: 9 which has 13.61% sequence identity to the amino acid sequence shown in SEQ ID NO: 2. In some embodiments, the PtrXB37 polypeptide has an amino acid sequence as laid out in SEQ ID NO: 10 which has 51.90% sequence identity to the amino acid sequence shown in SEQ ID NO: 2. In some embodiments, the PtrXB39 polypeptide has an amino acid sequence as laid out in SEQ ID NO: 11 which has 73.28% sequence identity to the amino acid sequence shown in SEQ ID NO: 2.

In some embodiments, the exogenous nucleic acid is stably integrated into the plant genome. Stably transformed cells typically retain the introduced nucleic acid with each cell division. The stably transformed genetically modified plants, plant cells or plant tissue can be useful in the methods described herein.

In some embodiments, the nucleotide sequence is operably linked to a heterologous promoter. The heterologous promoter can be a constitutive promoter, an inducible promoter, or a native promoter. In some embodiments, the heterologous promoter is a 35S promoter.

In some embodiments, the plant is a monocot or a dicot. In some embodiments, genetically modified plant is selected from the group consisting of genera *Acer, Afzelia, Allium, Arabidopsis, Agrostis, Avena, Betula, Brassica, Capsicum, Citrullus, Cucumis, Eucalyptus, Fagus, Festuca, Fraxinus, Fragaria, Glycine, Gossypium, Hordeum, Ipomoea, Jatropha, Juglans, Lemna, Lolium, Malus, Manihot, Medicago, Micropus, Milium, Miscanthus, Nicotiana, Oryza, Pennisetum, Phalaris, Phleum, Picea, Pinus, Poa, Populus, Prunus, Quercus, Rosa, Salix, Solanum, Sorghum, Spinacia, Tectona, Trifolium, Triticum, Panicum, Saccharum, Setaria, Zea*, and *Zoysia*. In some embodiments, the plant is *Populus*. In some embodiments, the plant is *Populus trichocarpa.*

Phenotypes of the Genetically Modified Plants

In some embodiments, the genetically modified plant, plant cell or plant tissue displays one or more of the following characteristics: has increased root development compared to a wild type plant, plant cell or plant tissue; has improved plant defense against pathogens by increasing production of ethylene and jasmonates compared to a wild type plant, plant cell or plant tissue; has increased flooding tolerance compared to a wild type plant; and has increased carbon dioxide ($CO_2$) absorption or carbon dioxide ($CO_2$) sequestration compared to a wild type plant, plant cell or plant tissue.

In some embodiments, the root development comprises adventitious root formation. By "increase in root development", it can include increase in root numbers and/or increase in root length from a genetically modified plant, plant cell or plant tissue, as compared to a control plant, plant cell or plant tissue without the genetic modification. The extent of increase, e.g., in the number of roots, can be at least 20%, 30%, 40%, 50%, 100% (2 fold), 3 fold, 4 fold, 5 fold, 10 fold, 15 fold, or greater. In some embodiments, the increase is at least 2 fold. In some embodiments, the increase is at least 5 fold. In some embodiments, the increase is at least 10 fold.

In some embodiments, the genetically modified plant, plant cell or plant tissue disclosed herein displays improved plant defense against pathogens by increasing production of ethylene and jasmonates compared to a wild type plant, plant cell or plant tissue. Pathogens can include, for example, *Pseudomonas syringae* pv *tomato* DC3000. Production of ethylene and jasmonates can be determined by using known methodology, for example, laser-based photoacoustic detector and liquid chromatography tandem mass spectrometry (LC-MS/MS), respectively. The extent of increase can be, e.g., at least 10%, at least 20%, at least 30%, at least 40%, at least 50%, at least 75%, at least 100%, or greater.

In some embodiments, the genetically modified plant, plant cell or plant tissue disclosed herein displays improved flooding tolerance compared to a wild type plant, plant cell or plant tissue. Flooding tolerance can be achieved by gas exchange under flooding conditions, and thus increased flooding tolerance can be determined based on increased gas exchange under flooding conditions, as illustrated in the Examples hereinbelow. The extent of increase can be, e.g., at least 10%, at least 20%, at least 30%, at least 40%, at least 50%, at least 75%, at least 100%, or greater.

In some embodiments, the genetically modified plant, plant cell or plant tissue disclosed herein displays increased flavonoids in roots, thereby increasing the resilience of the plant roots to environmental stresses compared to a wild type plant, plant cell or plant tissue. The levels of flavonoids in roots can be measured by known methodologies, e.g., Gas Chromatography-Mass Spectrometry (GC-MS). The extent of increase can be, e.g., at least 10%, at least 20%, at least 30%, at least 40%, at least 50%, at least 75%, at least 100%, or greater.

Flavan-3-ols, such as catechin and epicatechin, are crucial compounds for plants to adapt to biotic and abiotic stresses. In some embodiments, three flavan-3-ols are significantly increased in the roots of genetically modified plants. In some embodiments, PtrXB38 affects flavonoid biosynthesis in roots. In some embodiments, the higher abundances of flavonoids increase the resilience of the genetically modified plant roots to environmental stresses.

Methods

In some embodiments, disclosed herein is a method of increasing root development in a plant, plant cell or plant tissue. The method comprises introducing into the plant, plant cell or plant tissue, an exogenous nucleic acid sequence encoding a PtrXB38 polypeptide or a homolog thereof, thereby obtaining a genetically modified plant, plant cell or plant tissue, wherein the genetically modified plant, plant cell or plant tissue displays an enhanced expression of the PtrXB38 polypeptide or the homolog thereof and an increase in root development compared to a wild type plant, plant cell, or plant tissue.

In some embodiments, disclosed herein is a method of improving plant defense against pathogens in a plant, plant cell or plant tissue comprising enhancing expression of a PtrXB38 polypeptide or a homolog thereof in the plant, plant cell or plant tissue, thereby increasing production of ethylene and jasmonates compared to a wild type plant.

In some embodiments, disclosed herein is a method of increasing flooding tolerance in a plant, plant cell or plant tissue comprising enhancing expression of a PtrXB38 polypeptide or a homolog thereof in the plant, plant cell or plant tissue, thereby increasing root development compared to a wild type plant.

In some embodiments, disclosed herein is a method of increasing carbon dioxide ($CO_2$) absorption or carbon dioxide ($CO_2$) sequestration in a plant, plant cell or plant tissue comprising enhancing expression of a PtrXB38 polypeptide or a homolog thereof in the plant, plant cell or plant tissue, thereby increasing root development compared to a wild type plant.

In any of the methods, enhanced expression of a PtrXB38 polypeptide or a homolog thereof in a plant, plant cell or plant tissue can be achieved by introducing an exogenous nucleic acid encoding the PtrXB38 polypeptide or a homolog thereof, as described herein, into the plant, plant cell or plant tissue.

Unless defined otherwise, all technical and scientific terms used herein have the same meaning as commonly understood by one skilled in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

The specific examples listed below are only illustrative and by no means limiting.

EXAMPLES

Example 1: eQTL Mapping

Whole-genome resequencing and variant calling for the 917 *P. trichocarpa* individuals was performed as described previously (Yates, T. B. et al., *Genome Biol Evol* 13, 1-14, 2021). The single nucleotide polymorphism (SNP) and indel dataset is available at Bioenergy Center website. A total of 390 and 444 RNA-Seq samples in leaf and xylem, respectively, were used to perform eQTL analysis. Prepublication RNA-seq data was made available for this study courtesy of the Center for Bioenergy Innovation and the Joint Genome Institute. Briefly, leaf and xylem tissue were collected in 2015 from 4-year-old trees at the Clatskanie, OR field site and processed as described previously (Zhang, J. et al., *New Phytologist* 220, 502-516, 2018). Reads were aligned to the *Populus trichocarpa* v. 3.1 reference (Tuskan, G. A. et al., *Science* 313, 1596-604, 2006) using STAR (Dobin, A. et al., *Bioinformatics* 29, 15-21, 2013). Fragments per kilobase of transcript per million mapped reads (FPKM) counts were then obtained for each genotype, resulting in a genotype-transcript matrix. The gene expression profiles were then used as phenotypes in GWAS analyses using EMMAX (Zhou, X. & Stephens, M., *Nat Genet* 44, 821-4, 2012). SNPs and indels with minor allele frequencies≥0.05 identified from whole-genome resequencing were used for this analysis. To account for multiple testing, the Bonferroni corrected threshold, $P \leq 0.05/8253066 = 6.06\times10^{-9}$, was used to determine statistical significance.

Figure 6:
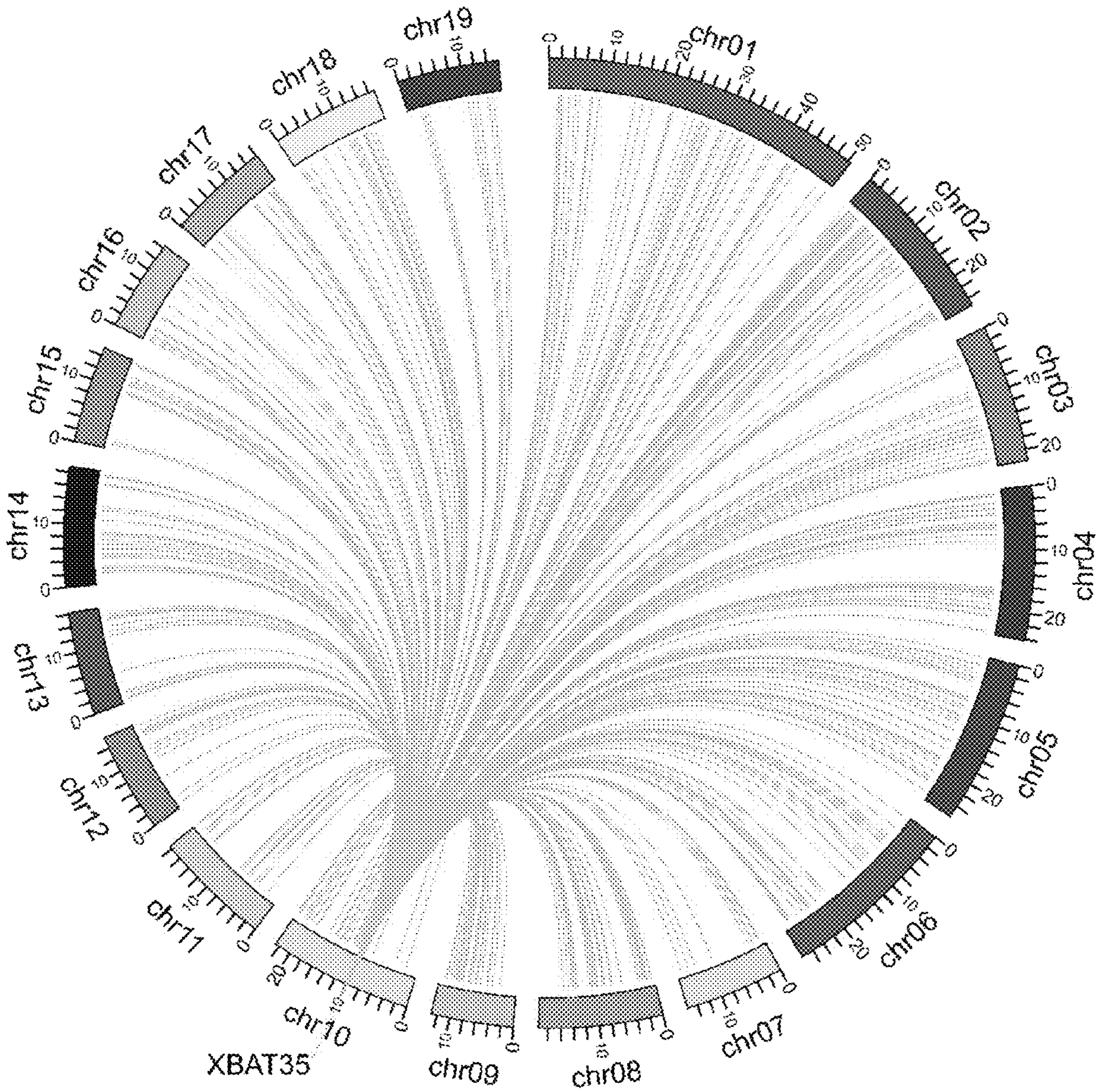
FIG. 6. Identification of PtrXB38 as a hotspot by eQTL mapping. Circos plot for eQTL hotspot of PtrXB38. The yellow lines show the connections between PtrXB38 and associated genes across different chromosomes. Colored boxes represent the different chromosomes.

Example 2: Genetic Mapping of the PtrXB38 Gene eQTL mapping was performed by correlating 390 mature leaf and 444 developing xylem transcriptomes to >8.2 million single nucleotide polymorphisms (SNPs) and small indels to identify putative cis- and trans-regulatory elements in the *Populus trichocarpa* GWAS mapping panel. A putative cis-regulatory element was identified that was associated with the expression of the *P. trichocarpa* gene model, Potri.010G070800, annotated as a PtrXB38 and was predicted to encode a C3HC4-type E3 ligase (FIGS. 1A-E). Moreover, this putative cis-element co-located with a trans-eQTL hotspot that was significantly associated with expression of more than 500 genes in developing xylem and mature leaf transcriptomes (FIG. 6). Specifically, 21 SNPs, encompassing a 20.83-kb interval, exhibited associations with expression levels of 492 genes in xylem tissue (P-values≤9.85E-11), while 10 SNPs within a 6.47-kb interval were significantly associated with expression of 81 genes in leaf tissue (P-values≤9.41E-11). PtrXB38 was the only annotated gene found in both intervals. In particular, SNP Chr10:9762348 was significantly associated with higher expression of PtrXB38 in developing xylem and leaf (FIGS. 1F, G), as well as expression levels of its putative targets described below.

Figure 1T:
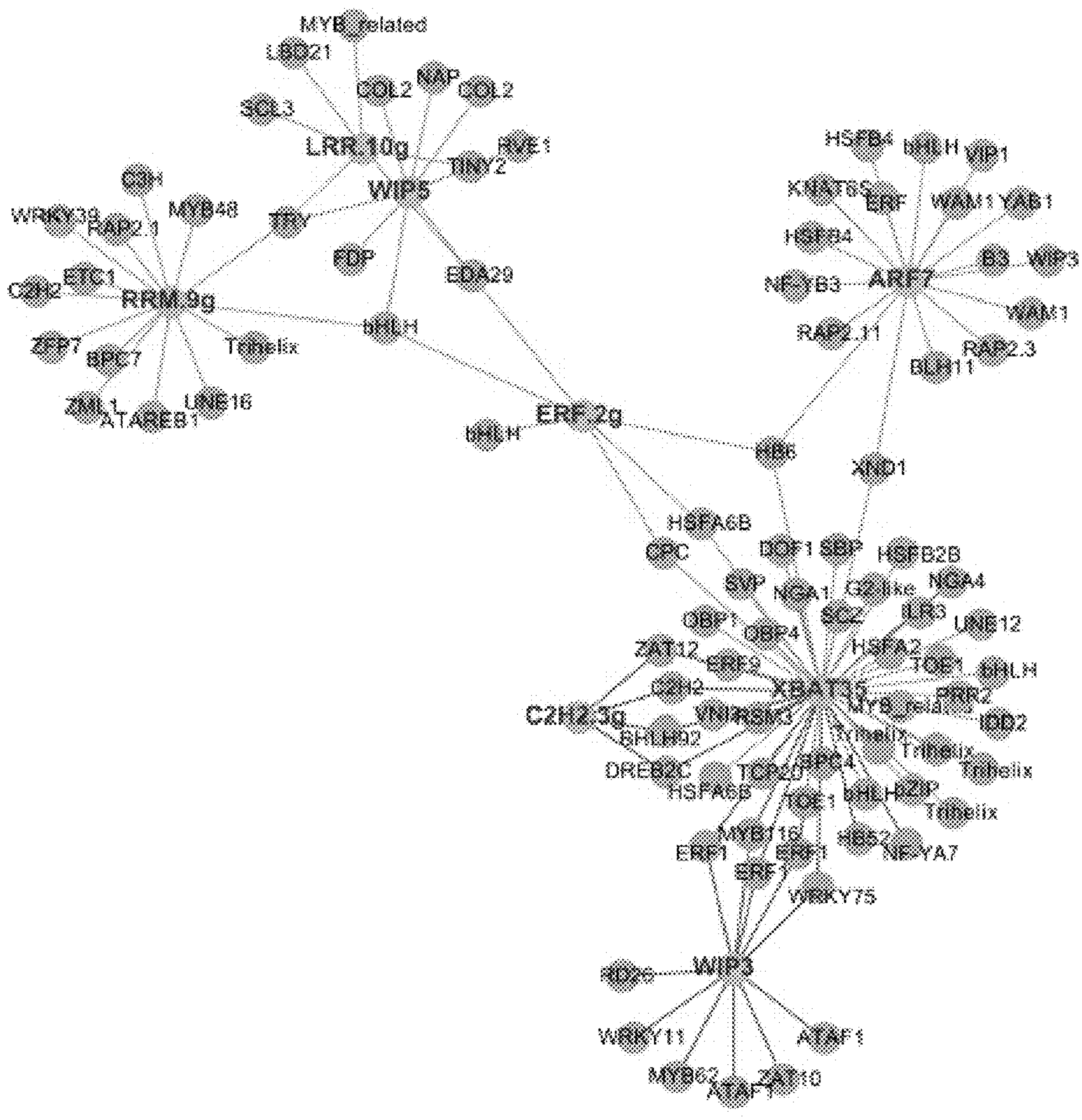

Among putative targets for the PtrXB38 trans-eQTL were 73 and 18 transcription factors expressed in xylem and leaf, respectively. These included multiple members of the MYB, AP2/ERF, HSF, bHLH, GT and NAC families. Multiple transcription factor families and their putative downstream targets were previously implicated in plant organ development. Examples include genes previously implicated in callus formation and root development, such as SCZ and OBP4 (Ramirez-Parra, E. et al., *New Phytologist* 213, 1787-1801, 2017; Ten Hove, C. A. et al., *Current Biology* 20, 452-457, 2010) as well as regulators of root growth and xylem development, such as TCP20 and SVP (Zhang, J. et al., *Nat Plants* 5, 1033-1042, 2019; Li, C. et al., *Proceedings of the National Academy of Sciences of the United States of America* 102, 12978-12983, 2005) (FIGS. 1H-O). Transcript abundance of these genes was significantly associated with SNPs within the PtrXB38 locus including Chr10:9762348 mentioned above (FIGS. 1P-S). Given robust numbers of putatively co-regulated genes in xylem and leaf, a three-layer network was constructed by assessing shared targets among these transcription factors that were associated with the PtrXB38. This overlap suggested that those shared targets may be regulated by PtrXB38 via these transcription factors. This resulted in a network of putatively co-regulated gene modules falling under the overall regulation of PtrXB38 (FIG. 1T). On one hand, ARF and ERF transcription factors served as two high-rank nodes in the regulatory network, suggesting plant hormones, especially auxin and ethylene signaling pathways, may be involved in PtrXB38-regulated developmental processes (FIG. 1T). On the other hand, the MYB and bHLH were identified as direct subordinated transcription factors, suggesting that PtrXB38 may regulate MYB/bHLH-mediated biological processes, such as secondary metabolism (FIG. 1S) (Xu, W., *Trends in Plant Science* 20, 176-185, 2015).

Example 3: PtrXB38 Promotes the Formation of Adventitious Roots

Figures 2A, 2B, 2C, 2D, 2E, 2F, 2G, 2H, 2I, 2J:
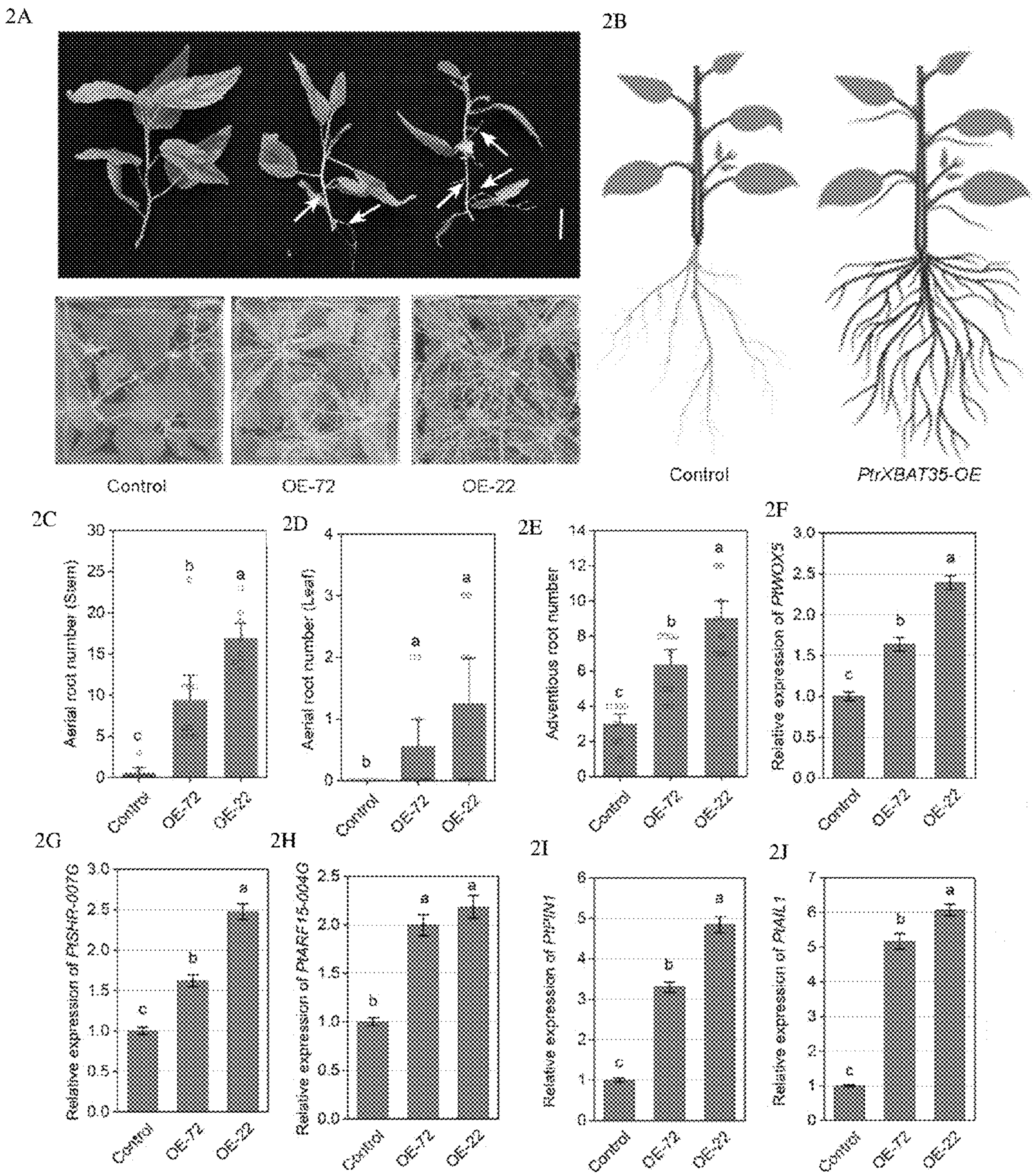
FIGS. 2A-2J. Over-expression of PtrXB38 promotes adventitious root formation in poplar. (A) Morphological phenotypes of adventitious root formation in control and two PtrXB38-OE independent lines, OE-72 and OE-22. The arrows denote the adventitious roots developed from stem or leaf, bar=1 cm. (B) Schematic representation of aerial and below-ground root systems in control and PtrXB38-OE plants. (C, D) Aerial root numbers of control and two PtrXB38-OE lines on stem (C) and leaf (D). (E) Adventitious root numbers of control and two PtrXB38-OE lines. (F-J) Expression of adventitious root development related genes WOX5 (F), SHR (G), ARF15 (H), PIN1 (I), and AIL1 (J) in control and PtrXB38-OE micro-propagated cuttings. Bar charts represent mean±s.e.m ($n \geq 3$ independent plants), and different letters represent significant difference between groups ($p \leq 0.05$) determined by one-way ANOVA followed by Tukey's test.
Figure 7A:
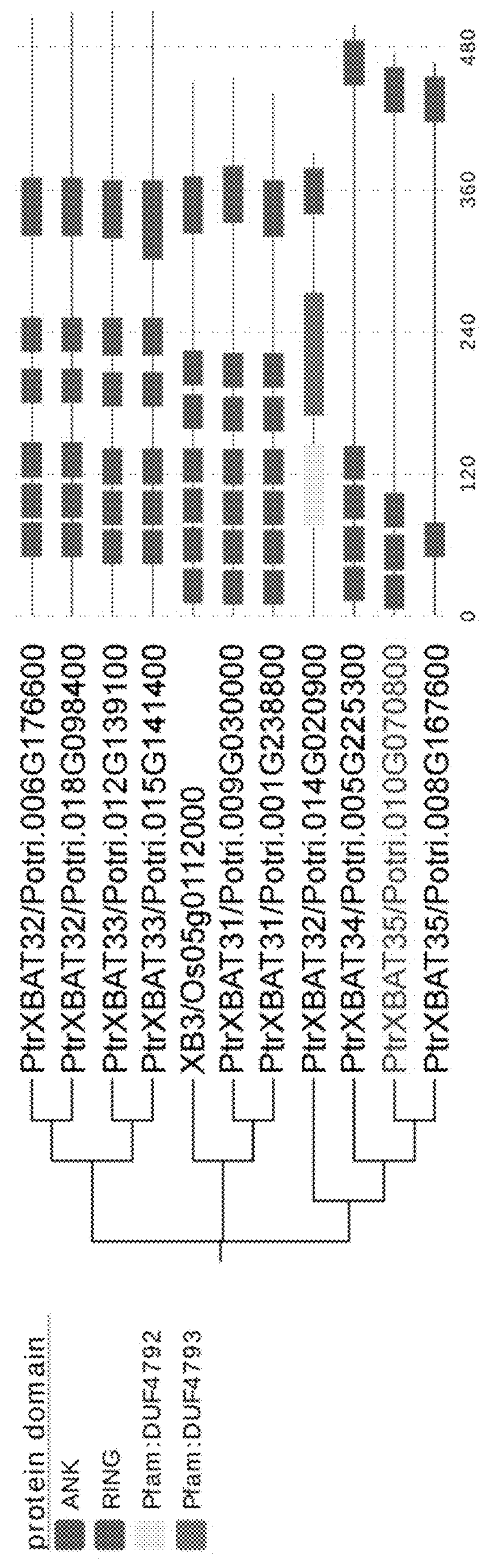
FIGS. 7A-7B. Protein domains and tissue expression patterns of PtrXBAT genes. (A) Domain structures of XBAT family in *Populus trichocarpa*. Rice XB3 protein was used as a template. (B) Tissue expression patterns of XBAT gene family in *Populus trichocarpa*. The expression data of different tissues was obtained from *Populus* Gene Express Atlas.
Figure 7B:
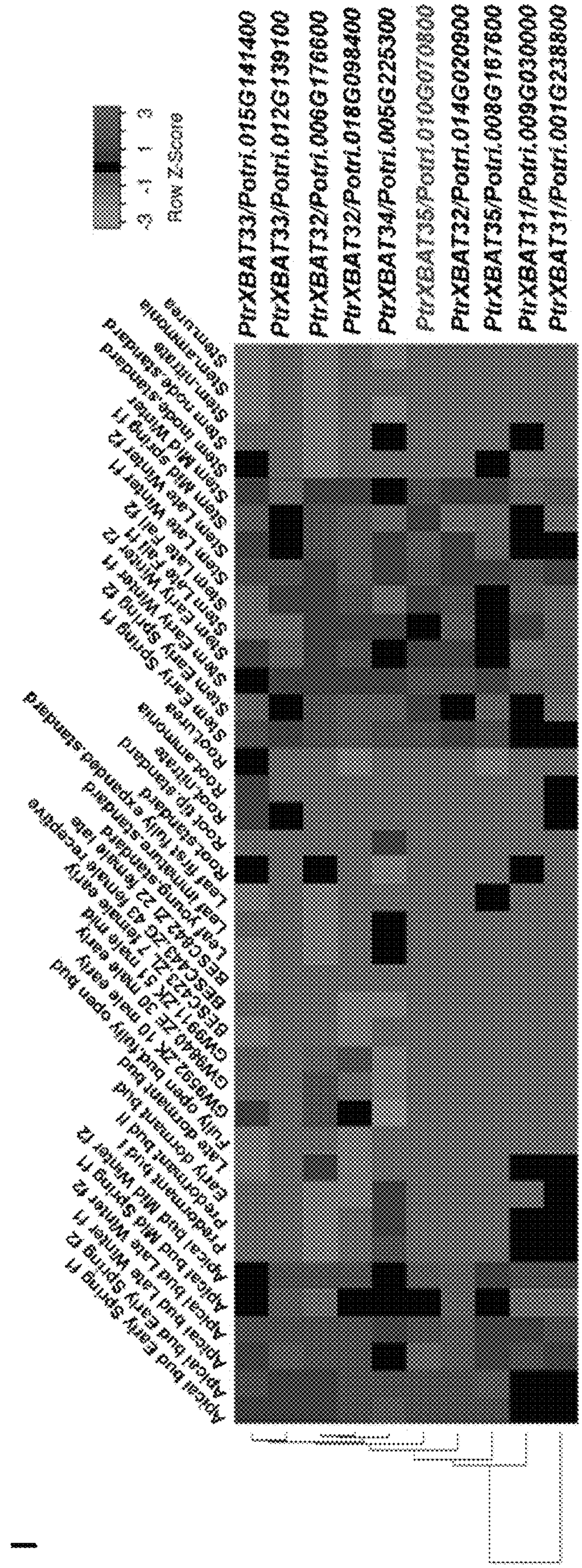
Figure 8:
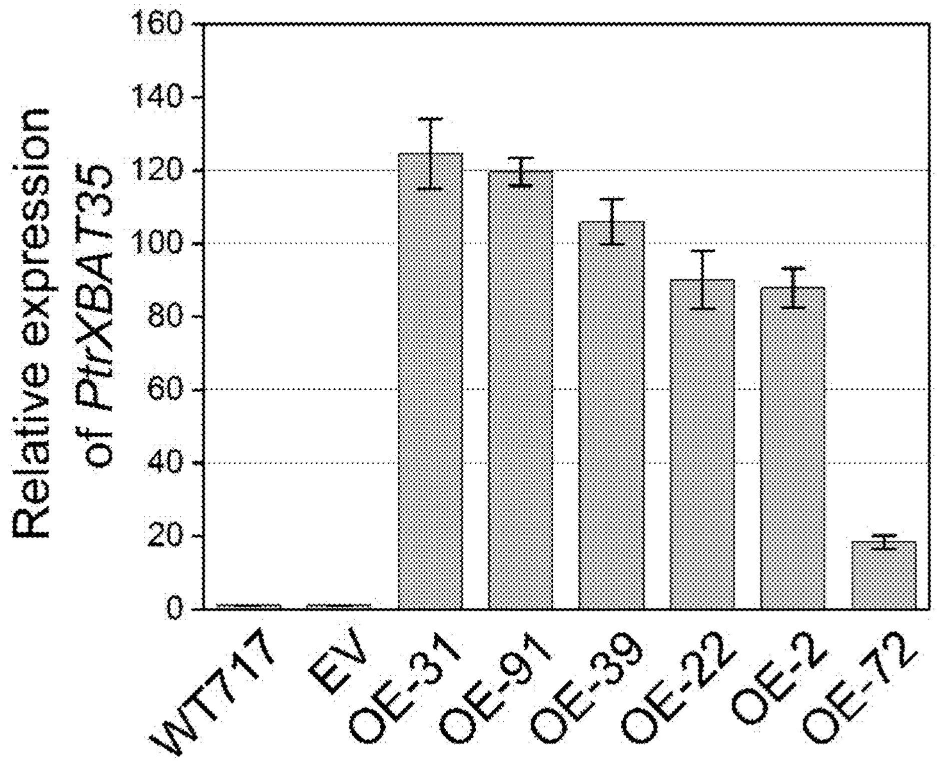
FIG. 8. Expression levels of PtrXB38 in independent lines of PtrXB38-OE transgenic plants. Total RNA was extracted from leaves of one-month-old *Populus* plants for qRT-PCR analysis. Bar charts represent mean±s.e.m (n=3 independent plants).
Figures 9A, 9B:
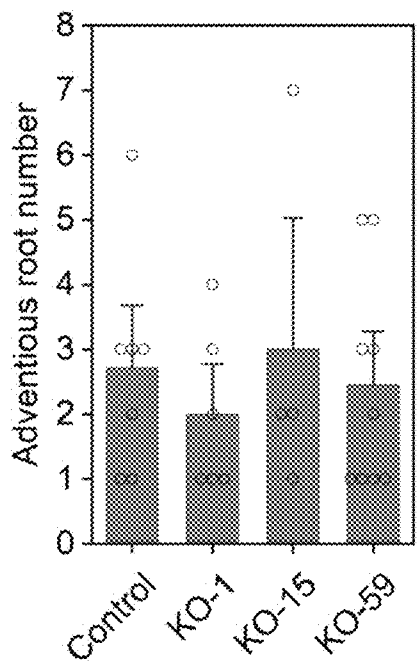
FIGS. 9A-9B. Adventitious root numbers of PtrXB38-KO plants. (A) Mutation patterns of XB38 alleles in three independent CRISPR/Cas9 lines. The nucleotide length change of indel is indicated in red. The PtrXB38 gene is present as tandem duplicate in *P. tremula*×*P. alba* 'INRA 717-1B4' based on the draft genome assembly and hence four alleles are shown. 'a' represents the alternative subgenome copies, and 'p' represents the main/primary subgenome copies. (B) adventitious root number of control and PtrXB38-KO lines. Bar charts represent mean±s.e.m.

Given the number of developmental regulators implicated in the predicted PtrXB38 regulatory network, its function was assessed by generating and characterizing overexpression (OE) and knock-out (KO) transgenic plants in the *P. tremula×P. alba* 'INRA 717-1B4' background. Two independent lines, OE-72 and OE-22, in which the expression of PtrXB38 was 18- to 90-fold higher compared to empty vector control, were selected for further analyses (FIG. 8). In contrast to the control plants, PtrXB38-OE plants not only developed larger and more prolific ARs, but also produced more aerial roots (FIGS. 2A-D). When micro-propagated synchronously in ½ MS medium, PtrXB38-OE plants generated 6 to 12 ARs compared to 3 ARs in control plants. AR formation in the OE lines was also correlated with the PtrXB38 transgene expression level (FIG. 2E and FIG. 8). Alternatively, knock-out mutants of PtrXB38 did not show any difference in AR formation when compared to control (FIGS. 9A-9B). It is hypothesized that this is due to the genetic redundancy of the XBAT gene family, as there are eleven members in *Populus* (FIGS. 6 and 7A) and two of them have previously been reported to be involved in root development (Trupiano, D. et al., *Planta* 238, 271-282, 2013; Song, Y. et al., *Journal of Experimental Botany,* 2020).

Considering the significant differences in AR formation between OE transgenics and empty vector controls, transcriptional responses of known AR regulators using qRT-PCR analysis were assessed. As an early-stage regulator of AR formation, PtWOX5, which is expressed in the stem cell niche and is required for maintaining root meristem activity (Li, J. et al., *Tree Physiology* 38, 139-153, 2017), was highly up-regulated in PtrXB38-OE plants (FIG. 2F). Additionally, transcript levels of PtWOX5's upstream activator, PtSHR (Xuan, L. et al., *Plant Cell, Tissue and Organ Culture* (*PCTOC*) 117, 253-264, 2014), were also significantly increased in the PtrXB38-OE plants (FIG. 2G). Expression of PtrAIL1, another AP2/ERF family transcription factor gene responsible for root meristem and primordium formation (Rigal, A. et al., *Plant Physiol* 160, 1996-2006, 2012), was likewise significantly increased in PtrXB38-OE (FIG. 2J). Both WOX5 and AIL1 were reported to be involved in auxin-dependent AR development (Druege, U. et al., *Frontiers in Plant Science* 7, 2016). In line with this view, it was found that PtrXB38-OE resulted in up-regulation of auxin signaling and transport genes PtARF15 and PtPIN1 (FIG. 2H, I).

Example 4: Generation of PtrXB38-OE and -KO Plants in *Populus*

The full-length coding sequence of PtrXB38 was PCR amplified from xylem cDNA of *P. trichocarpa* 'Nisqually-1' and assembled into binary vector p201N-Cas9 (Addgene plasmid 59175) (Jacobs, T. B. et al., *BMC Biotechnol* 15, 16, 2015) to replace SpCas9 behind the double 35S promoter using NEBuider HiFi DNA assembly cloning kit (New England Biolabs). The generation and genotyping of PtrXB38-KO transgenic *Populus* plants in *Populus tremula*× *alba* 'IRNA 717-1B4' followed the methods as described (Tsai, C.-J. et al., *Plant Physiol* 183, 123-136, 2020). To generate the PtrXB38 knockout construct, SwaI-digested p201N-Cas9 vector was PCR amplified by Q5 High-Fidelity DNA Polymerase (New England BioLabs) with primers. The MtU6.6 promoter and scaffold fragments were also PCR amplified from the pUC-gRNA shuttle vector (Addgene plasmid 47024) (Jacobs, T. B. et al., *BMC Biotechnol* 15, 16, 2015) using tailed primers overlapping with p201N. The p201N-Cas9 vector, U6.6 promoter, scaffold and a pair of tailed primers containing the gRNA sequence were then assembled together using NEBuilder HiFi DNA Assembly Cloning Kit (New England Biolabs). Both constructs were fully sequenced, and heat-shock transformed into *Agrobacterium tumefaciens* strain C58/GV3101 (pMP90). The *Populus* transformation and regeneration was performed as described (Tsai, C.-J. et al., *Plant Physiol* 183, 123-136, 2020) with the following modifications: shoot elongation media contained 0.05 mg/L 6-benzylaminopurine, all media were additionally supplemented with 200 mg/L L-glutamine and solidified with 3 g/L gellan gum, leaf discs following cocultivation were washed with 200 mg/L cefotaxime and 300 mg/L timentin, and transformants were maintained on appropriate media supplemented with 100 mg/L kanamycin, 200 mg/L cefotaxime and 300 mg/L timentin.

Mutation patterns were determined by amplicon sequencing as described (Tsai, C.-J. et al., *Plant Physiol* 183, 123-136, 2020). Gene-specific degenerate primers flanking both on-target (Potri.010G070800) and off-target (genome duplicate Potri.008G167600) sites were used for the first PCR, followed by PCR-barcoding, both using GoTaq G2 Green Master Mix (Promega). The pooled amplicon library was quantified by a Qubit Fluorometer (Invitrogen) prior to be sequenced on an Illumina MiSeq using a Nano PE150 flow cell at the Georgia Genomics and Bioinformatics Core, University of Georgia. After de-multiplexing, data were analyzed by the AGEseq program (Tsai, C.-J. et al., *Plant Physiol* 183, 123-136, 2020).

Figure 10A:
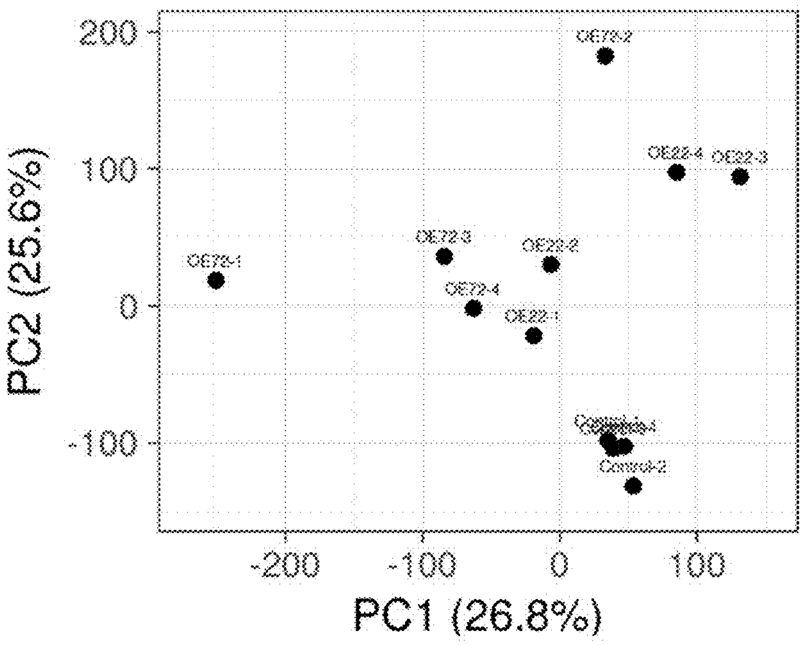
FIGS. 10A-10B. Overexpression of PtrXB38 alters the *Populus* transcriptome in roots. (A) Principal component analysis of the transcriptome data. X and Y axis show principal component 1 and principal component 2 that explain 26.8% and 25.6% of the total variance, respectively. N=12 data points. (B) Abundance profile of Potri.010G070800.6 transcript (annotated was PtrXB38). Bar charts represent mean±s.e.m, and different letters represent significant difference between groups (P≤0.05) determined by one-way ANOVA followed by Tukey's test.
Figure 10B:
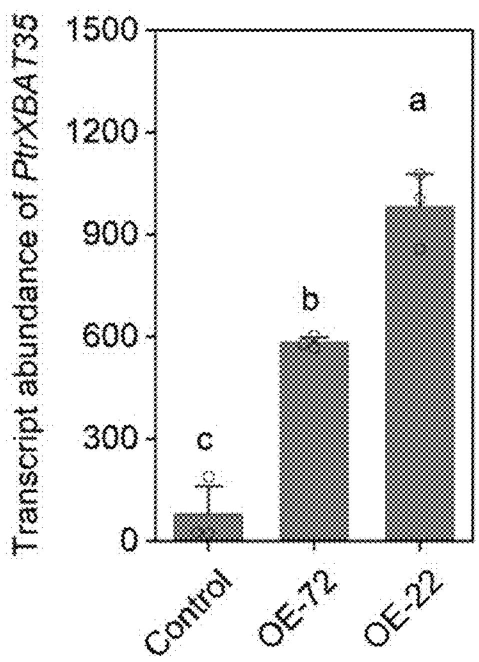
Figure 11:
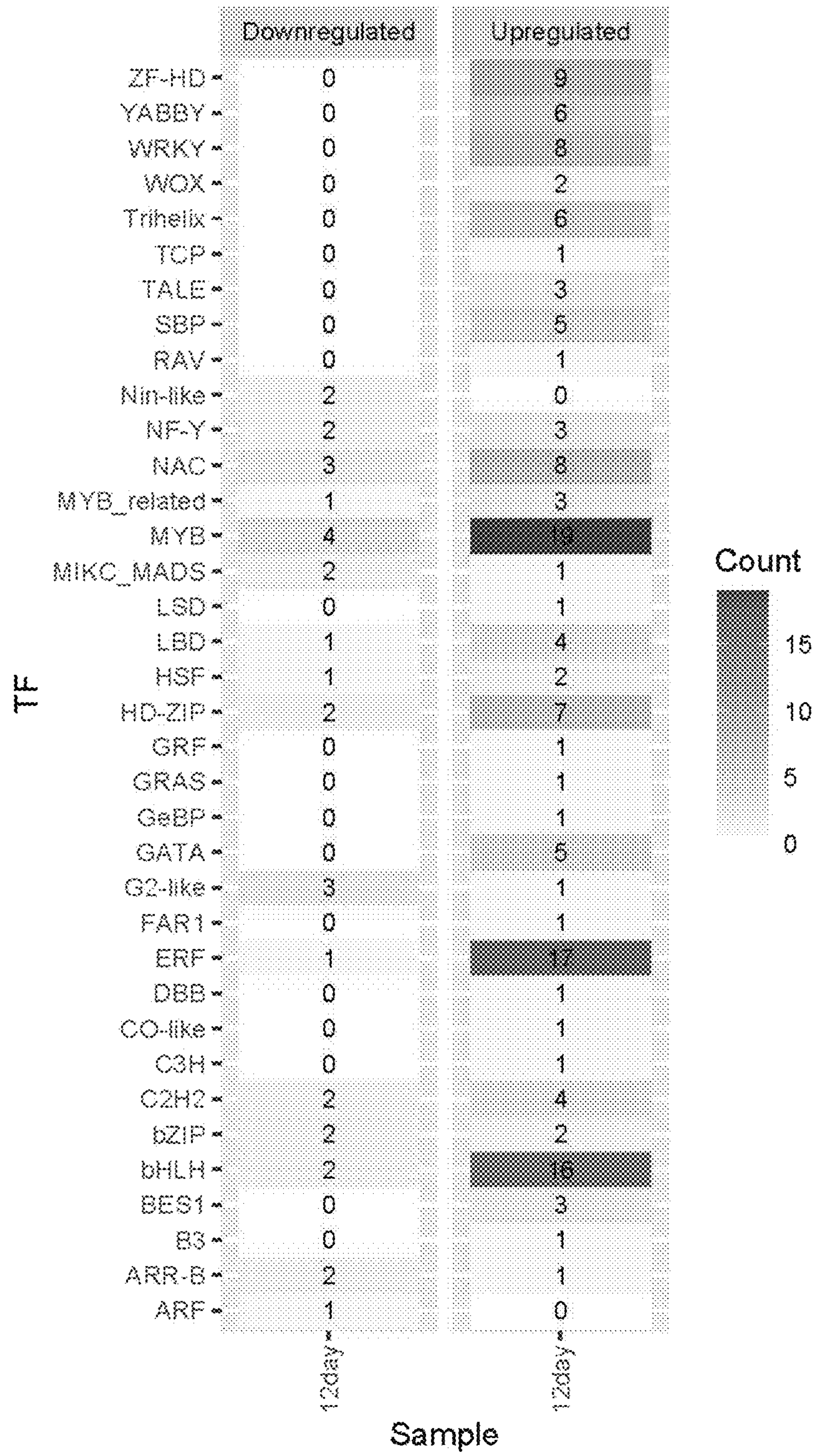
FIG. 11. Expression of transcription factor family genes regulated by PtrXB38. Number of TF coding gene among DEGs from RNA-seq results were counted in 12-day-old root tissue.
Figure 13A:
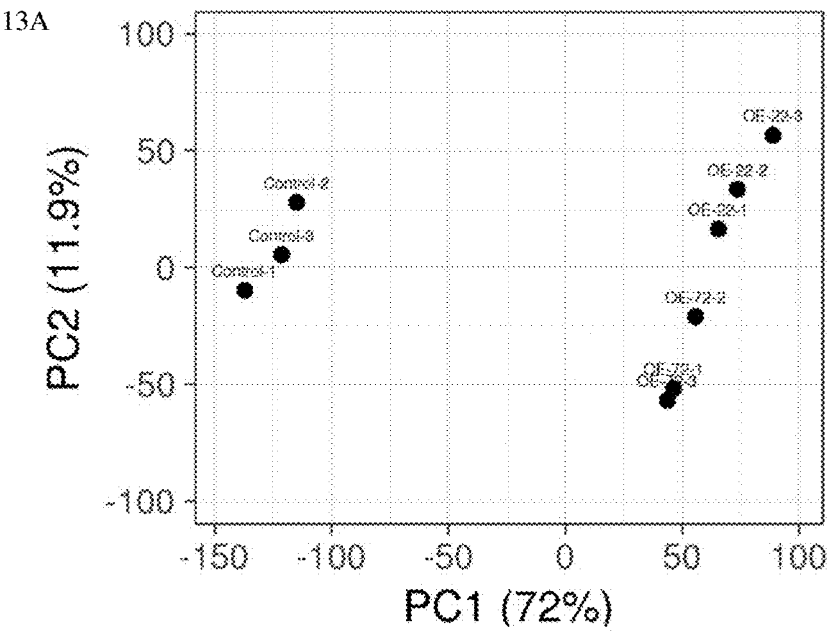
FIGS. 13A-13B. Overexpression of PtrXB38 alters the *Populus* proteome in roots. (A) Principal component analysis of the proteome data. X and Y axis show principal component 1 and principal component 2 that explain 72% and 11.9% of the total variance, respectively. N=9 data points. (B) Abundance profile of Potri.010G070800.6 protein (annotated was PtrXB38). Bar charts represent mean±s.e.m, and different letters represent significant difference between groups (P≤0.05) determined by one-way ANOVA followed by Tukey's test.
Figure 13B:
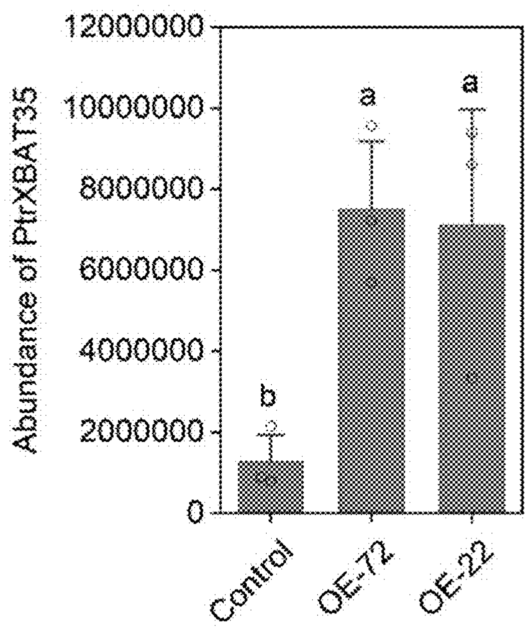

Example 5: Involvement of Auxin and Ethylene Signals in PtrXB38-Mediated Adventitious Root Formation To better understand the molecular mechanism of PtrXB38 in the regulation of root development, transcriptome and proteome analyses were performed to identify changes in gene expression and protein abundance in the roots of 12-day-old PtrXB38-OE plants. Principal component analysis revealed separate clustering of the two PtrXB38-OE lines from the control group, reflecting the global transcriptomic and proteomic changes induced by over-expression of PtrXB38 (FIGS. 10A and 13A). Both transcript level and protein abundance of PtrXB38 shown by RNA-seq and proteomics results confirmed that lines OE-72 and OE-22 are bona fide PtrXB38-OE plants (FIGS. 10B and 13B). Both transcriptome and proteome analyses confirmed the upregulation of a large number of TF families, such as MYB, ERF, and bHLH, supporting the identification of PtrXB38 as a trans-eQTL hotspot (FIG. 11).

Figure 12A:
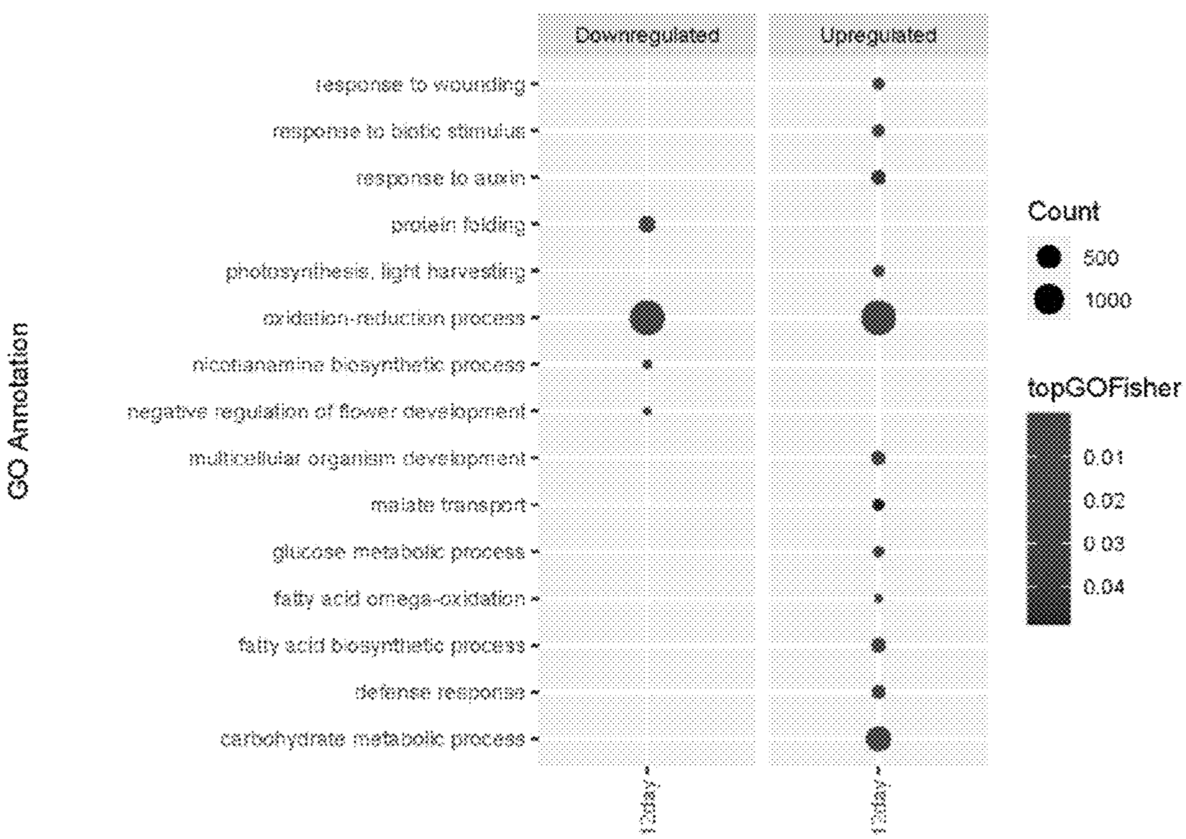
FIGS. 12A-12B. Functional category enrichment of the DEGs. (A-B) GO annotation (A) and KEGG pathway (B) analyses for the DEGs in 12-day-old PtrXB38-OE root tissues.
Figure 12B:
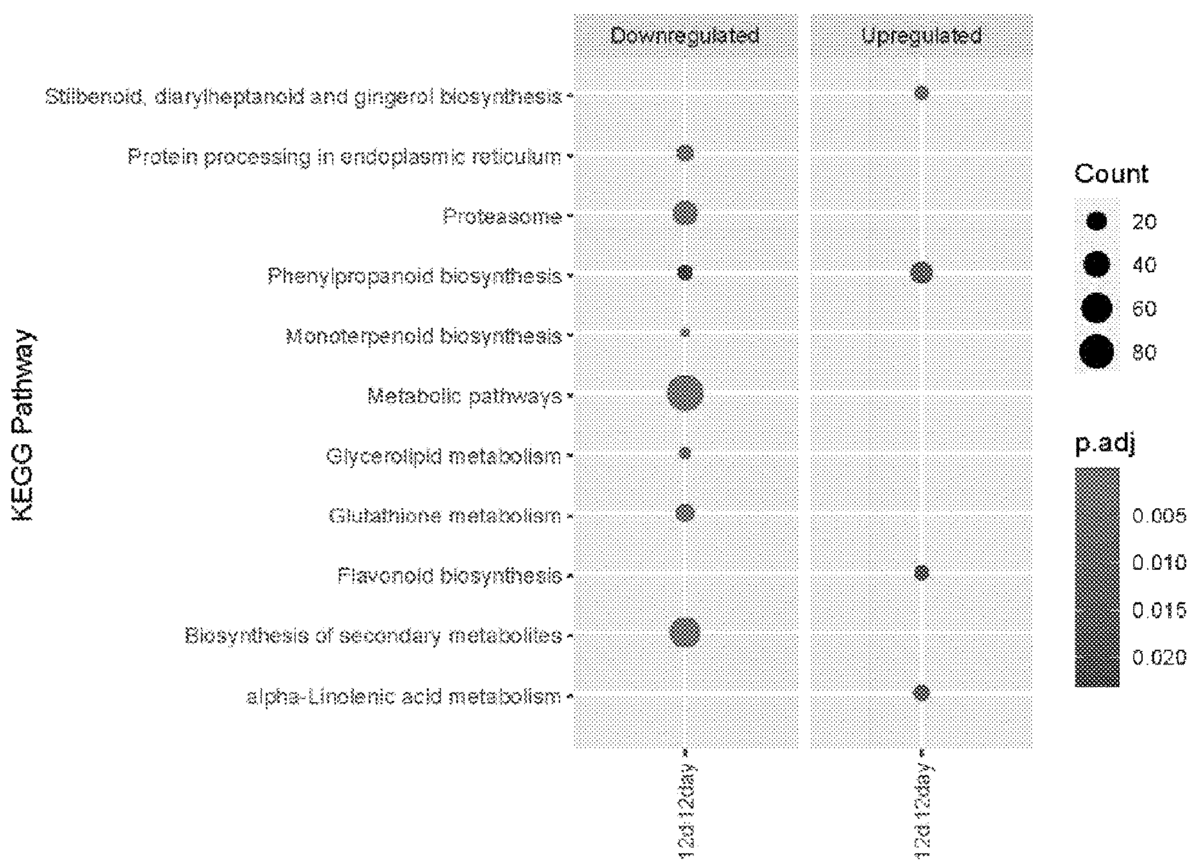
Figure 14:
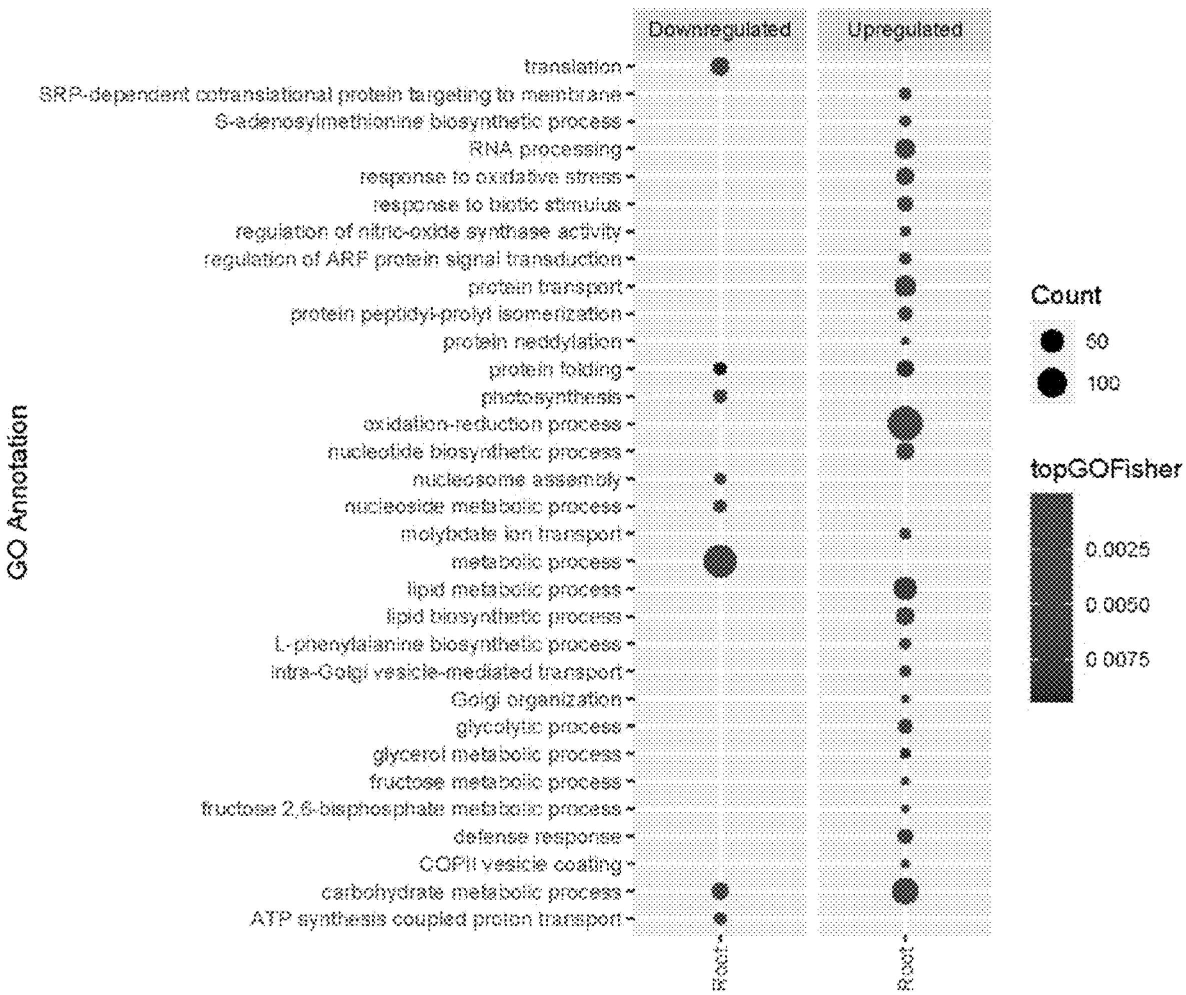
FIG. 14. Functional category enrichment of the DEPs. Results from GO annotation analysis are shown.
Figures 15A, 15B, 15C, 15D:
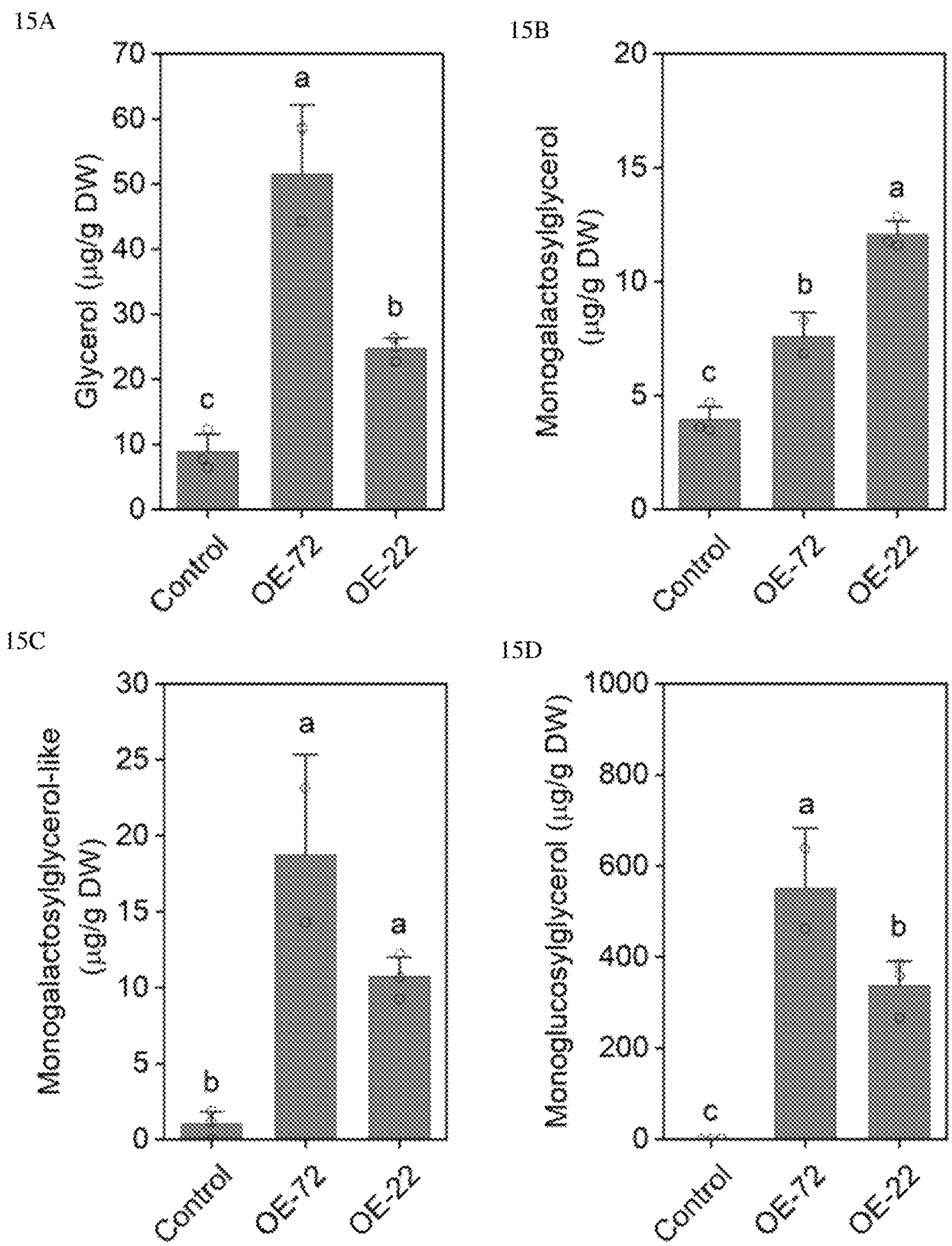
FIGS. 15A-15D. Glycerolipid content in PtrXB38-OE transgenic plants. Metabolite abundance of glycerol (A), monogalactosylglycerol (B), monogalactosylglycerol-like (C), and monoglucosylglycerol (D). Bar charts represent mean±s.e.m, and different letters represent significant difference between groups (P≤0.05) determined by one-way ANOVA followed by Tukey's test.

The differentially expressed genes/proteins (DEGs/DEPs, FDR≤0.05) were further analyzed by Gene Ontology (GO) and KEGG pathway enrichments. GO terms "response to wounding", "response to auxin", and "multicellular organism development" were overrepresented. Similarly, "regulation of ARF protein signal transduction" was also enriched among the DEPs (FIG. 14). These results are consistent with previous eQTL predictions and support the idea that PtrXB38 regulation of root development involves wounding response and auxin signaling (FIG. 12A-B). This insight is corroborated by the findings of auxin biosynthesis, signaling pathway, transport, and response related genes/proteins were highly induced in PtrXB38-OE plants from transcriptome and proteome profiling. Notably, ARF proteins were significantly accumulated in the PtrXB38-OE root samples (FIGS. 3A, B). To further verify the contribution of auxin signaling in PtrXB38-controlled root development, an auxin transport inhibitor NPA was applied during root formation. It was found that 5 μM NPA completely blocked root formation in both control and PtrXB38-OE micro-cuttings, and the promotive effect of PtrXB38 on AR formation was gradually attenuated by increasing NPA concentrations (FIGS. 3C, D). These results suggest that PtrXB38-regulated root development depends on auxin transport and signaling.

Figure 4C:
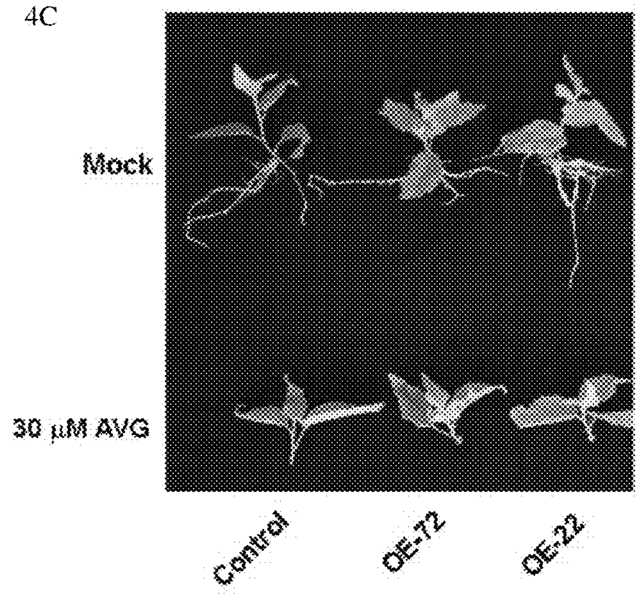
Figure 4D:
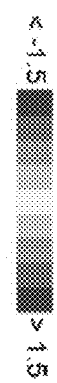
Figure 4E:
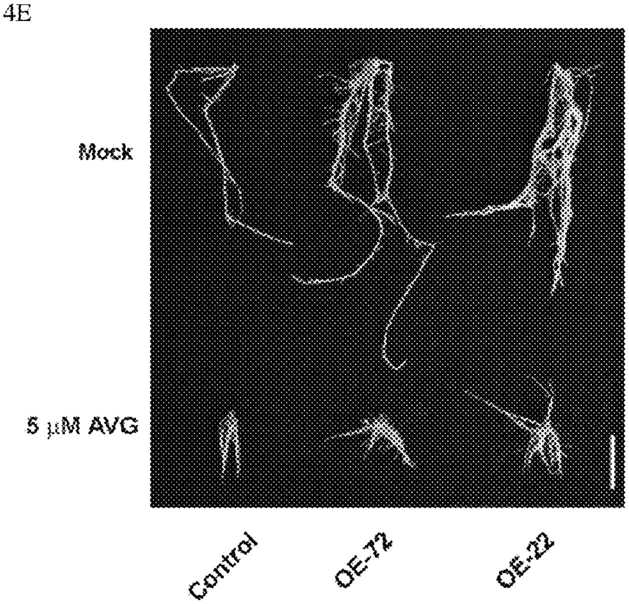
Figure 4F:
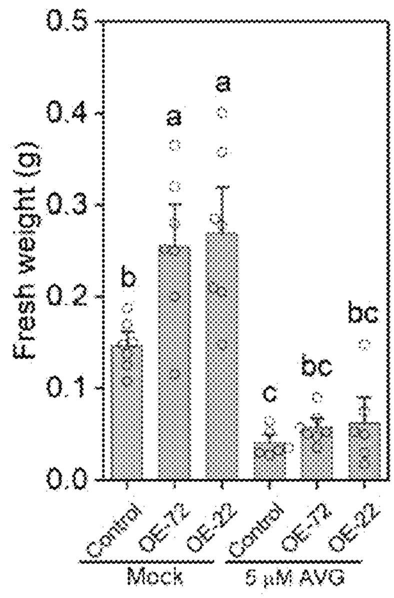

GO enrichment analysis for DEPs also identified proteins under the term "S-adenosylmethionine biosynthetic process", indicating PtrXB38 may affect ethylene biosynthesis (FIG. 14). In fact, it has been established that the E3 ligase XBAT32 specifically mediates ACS degradation through the ubiquitin/26S proteome pathway in *Arabidopsis* (Druege, U. et al., *Frontiers in Plant Science* 7, 2016; Prasad, M. E. et al., *Plant Physiol* 153, 1587-96, 2010). However, a decreased abundance of ACS proteins in PtrXB38-OE root samples was not observed. Instead, it was found that several ethylene biosynthesis related enzymes, such as SAMs and ACOs, were highly abundant (FIG. 4B). In addition to an increased transcript abundance (FIG. 4A), their elevated protein abundance might be indicative of protein stability regulation. Furthermore, many ERF genes were up-regulated in PtrXB38-OE root samples (FIG. 4D). All these lines of evidence suggest that PtrXB38 also enhances ethylene biosynthesis and signaling. This inference was supported by the observation that ethylene biosynthesis inhibitor, AVG, inhibited adventitious root formation at high concentrations and suppressed AR promotion by PtrXB38-OE at lower concentrations (FIGS. 4C, E, F). Therefore, it was concluded that both auxin and ethylene signaling are required for PtrXB38-mediated AR development. It is known that auxin and ethylene regulate each other's biosynthesis and signaling (Muday, G. K. et al., *Trends in Plant Science* 17, 181-195, 2012; Qin, H. & Huang, R., *International Journal of Molecular Sciences* 19, 3656, 2018), but it remains elusive whether it is the biosynthesis and signaling of auxin or ethylene that is directly regulated by PtrXB38. Future studies on identification of PtrXB38 direct targets may provide answers to this question. Strikingly, neither XB38-OE nor xb38 null mutant in *Arabidopsis* showed differences in root development, possibly indicating a functional diversity of XB38 between herbaceous and woody species (Carvalho, S. D. et al., *Mol Plant* 5, 1295-309, 2012).

Figures 5A, 5B, 5C, 5D, 5E, 5F, 5G, 5H:
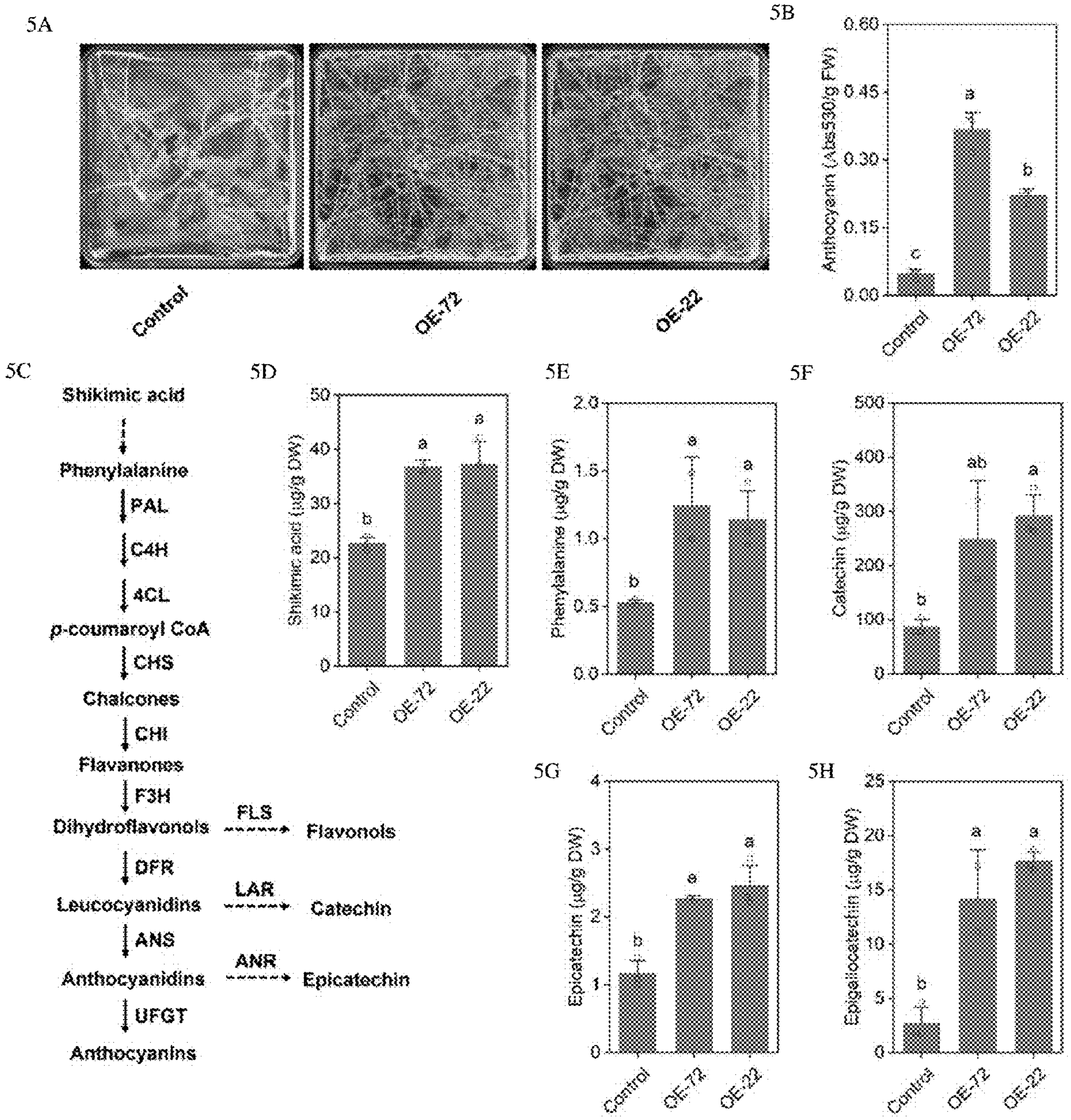

Example 6: PtrXB38 Increases Flavonoids in Roots, Plant Defense Against Pathogens, Flooding Tolerance and Carbon Dioxide ($CO_2$) Absorption or Sequestration It has been suggested that ethylene biosynthesis and signaling can affect secondary metabolism in plants (Buer, C. S. et al., *Plant physiology* 140, 1384-1396, 2006; Ke, S. W. et al., *Botanical Studies* 59, 11, 2018; Ma, W. et al., *Horticulture Research* 8, 43, 2021). The eQTL-predicted targets of PtrXB38, such as MYB and bHLH, are known to regulate secondary metabolism pathways, such as flavonoid biosynthesis (Constabel, C. P., *J Agric Food Chem* 66, 9882-9888, 2018). Therefore, PtrXB38 could play a role in the regulation of secondary metabolism. Indeed, MYB123 and bHLH42 were among the DEGs identified from the root of PtrXB38-OE plants, and KEGG and MapMan analysis of the DEGs and DEPs identified "flavonoid biosynthesis" and "glycerolipid metabolism" as overrepresented (FIG. 12B). The reddish coloration of mature roots of PtrXB38-OE plants also suggested possible accumulation of photoreactive metabolites. Therefore, metabolite profiling for the roots of PtrXB38-OE plants was performed. The increased abundance of anthocyanins could partially explain the brown or red colors of the OE roots (FIGS. 5A and 5B).

Figure 16A:
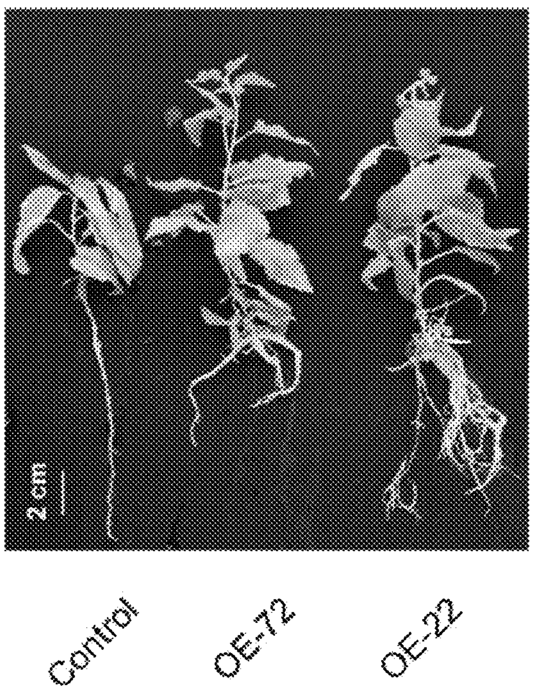
FIGS. 16A-16B. Growth advantage of PtrXB38-OE plants. (A) PtrXB38-OE saplings were grown in tissue culture medium for two months. (B) Fresh weigh of control and PtrXB38-OE plants. Bar charts represent mean±s.e.m, and different letters represent significant difference between groups (P≤0.05) determined by one-way ANOVA followed by Tukey's test.
Figure 16B:
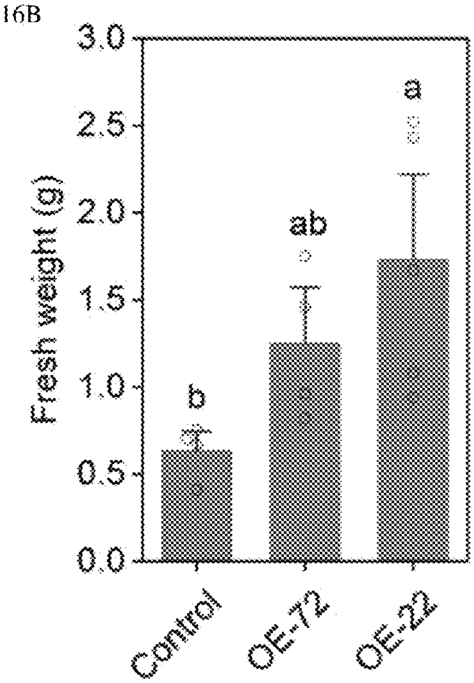

Flavan-3-ols, such as catechin and epicatechin, are crucial compounds for plants to adapt to biotic and abiotic stresses (Ullah, C. et al., *New Phytologist* 221, 960-975, 2019). Based on gas chromatography-mass spectrometry, three flavan-3-ols were significantly increased in the roots of PtrXB38-OE plants. Accordingly, the shikimate-phenylpropanoid pathway intermediates, shikimic acid and phenylalanine, were also significantly elevated in PtrXB38-OE roots (FIGS. 5C-5H). Although transcript elevation of phenylpropanoid and flavonoid biosynthetic genes were not observed, protein levels of PAL, 4CL, CHS, F3H, and ANS were significantly increased, indicating possible post-transcriptional regulations. Nonetheless, it was concluded that PtrXB38 affects flavonoid biosynthesis in roots. Consistent with the gene expression changes of glycerol metabolism in PtrXB38-OE plant roots, dramatic increases of glycerol, monoglucosylglycerol and monogalactosylglycerol were observed, while glycerol-1/3-phosphate content was reduced (FIG. 15A-D). The higher abundances of flavonoids and glycerolipids could increase the resilience of PtrXB38-OE plant roots to environmental stresses. In line with this view, the homologue of PtrXB38 in *Arabidopsis*, XB38 has been reported as an important regulator in biotic and abiotic stress response (Liu, H. et al, *Plant Physiology* 175, 1469-1483, 2017; Li, Q. et al., *The Plant Journal* 104, 1712-1723, 2020; Yu, F. et al., *Molecular Plant,* 2020). Taken together, root metabolic changes accompanied with root system enlargement suggest that PtrXB38 is an important regulator in root development and possibly also stress response (FIG. 16A-B).

PtrXB38-OE transgenic plant generated more adventitious and lateral roots especially fine roots in *Populus*. The changed root system facilitates plant nitrogen uptake, which requires more $CO_2$ absorption to fix the nitrogen. In addition, PtrXB38-OE transgenic poplars enhanced salicyl alcohol production, which can be served as carbon source for *Populus* beneficial microbial community. Enhanced root system provides more root-microbial interface. The rhizosphere microbiome in turn will promote plant nutrient and carbon uptake. Therefore, PtrXB38 can be a candidate gene to be engineered for carbon sequestration.

Recent advances reveal that phytohormone signaling contributes to shaping plant root architecture in both agronomic crops and bioenergy woody species (Csukasi, F. et al., *Biotechnology Journal* 4, 1293-1304, 2009; Depuydt, S. & Hardtke et al., *Current Biology* 21, R365-R373, 2011). Here, the present disclosure reports that a predicted E3 ligase gene, PtrXB38, identified by GWAS mapping, controls root development by regulating the biosynthesis and signaling of auxin and ethylene. The present disclosure showcases that eQTL genetic mapping, followed by functional validation, opens new prospects of discovering novel plant development regulators in woody plants (Zhang, J. et al., *New Phytologist* 220, 502-516, 2018; Labbé, J. et al., *Nature Plants* 5, 676-680, 2019; Muchero, W. et al., *Proceedings of the National Academy of Sciences* 115, 11573-11578, 2018).

Example 7: Materials and Methods

Plant Growth Conditions: The tissue culture plants were maintained in ½ MS media (½ MS basal salts, 20 g/L sucrose, 1× Gamborg's B5 vitamin mixture, 0.3% Gelzan) supplemented with 0.1 mg/L IBA and grown in growth chambers (16 h:8 h, light:dark) with white fluorescent light (100 $\mu mol\ m^{-2}\ s^{-1}$) at 22° C. To assess adventitious root development phenotype, 2-3 cm length of shoot tops from 1-month-old tissue culture saplings were excised and placed in fresh medium for root induction. Root number was counted 12 days after subculture. For chemical treatment, filter-sterilized auxin transport inhibitor naphthylphthalamic acid (NPA) and ethylene biosynthesis inhibitor aminoethoxyvinylglycine (AVG) were added in the ½ MS medium.

RNA Extraction and Quantitative RT-PCR Analysis: Total RNA was isolated from 7-day-old root samples using a Sigma plant total RNA kit according to the manufacturer's instructions. Reverse transcriptional reactions were performed using SuperScript III kit (Invitrogen) according to the manufacturer's instructions. Quantitative PCR was performed using a StepOne real-time PCR system (Thermo Fisher Scientific) and Maxima SYBR Green/ROX qPCR master mix (Thermo Fisher Scientific). PtEF1B was used as a reference gene in qRT-PCR and the gene expression level was calculated by the $2^{-\Delta\Delta CT}$ method.

Transcriptome Analysis: Total RNA was isolated from the 12-day-old root samples using the Sigma plant total RNA kit according to the manufacturer's instructions. Library construction and sequencing were performed using the DNBseq platform at BGI. The raw reads have been deposited at the SRA and can be accessed with the BioProject ID PRJNA785328. Clean reads were mapped to the *P. tremula*× *P. alba* clone INRA 717-1B4_v1.1 reference genome with STAR v2.6.1b (Dobin, A. et al., *Bioinformatics* 29, 15-21, 2013). FeatureCounts 1.6.3 in unstranded mode was used to generate raw gene counts, excluding multimapping reads (Zhou, X. & Stephens, M., *Nat Genet* 44, 821-4, 2012). The primary isoform of PtrXBAT35 (Potri.010G070800.6) in *P. trichocarpa* was manually curated to correct exon-intron prediction in the 717-1B4 v1.1 annotation. FPKM normalized counts were generated with RSEM, default parameters were used. DESeq2 v1.22.2 was used to identify differentially expressed genes (Love, M. I. et al., *Genome Biol* 15, 550, 2014). TopGO was used to generate gene ontology enrichments and KOBAS was used to generate KEGG enrichments (Alexa, A. et al., *Bioinformatics* 22, 1600-7, 2006; Xie, C. et al., *Nucleic Acids Res* 39, W316-22, 2011). Before visualization of pathways with MapMan 3.5.1.R2, Mercator4 v2.0 was used to annotate the 717-1B4 v1.1 proteome (Schwacke, R. et al., *Mol Plant* 12, 879-892, 2019).

Proteomics Analysis: The Protein identification and quantification of the poplar root samples were described previously (Wang, J. et al., *Comput Struct Biotechnol J* 19, 1917-1927, 2021) with minor modifications. Briefly, liquid nitrogen frozen and ground root tissue samples were solubilized in 1 mL lysis buffer (4% sodium dodecyl sulfate (SDS) with 10 mM dithiothreitol (DTT) in 100 mM ammonium bicarbonate (ABC)). Tissue samples were boiled in a heat-block for 5 min at 90° C., vortexed and boiled for an additional 5 min at 90° C. Samples were centrifuged at max speed for 5 min and supernatants were collected. Samples were then alkylated by incubating with 30 mM iodoacetamide for 15 min in dark to prevent reformation of disulfide bonds. Proteins were then extracted using a chloroform-methanol extraction protocol using methanol, chloroform, and LC/MS water in the ratio of 4:1:3. The protein layer was separated and washed using 100% methanol. Protein layer was air-dried, and this dried pellet was reconstituted in 3 mL sodium deoxycholate (SDC) solution made up of 1% SDC in 100 mM ABC. Protein concentration was measured using nanodrop (Thermo Scientific).

Each sample was adjusted to be 2 mg of total protein. Proteins were digested with two separate and sequential aliquots of sequencing grade trypsin (Promega) of 1:50 (wt/wt) protein:trypsin ratio. Samples were first digested for 3 hours, followed by overnight digestion. After digestion, SDC was removed by precipitating with 1% formic acid followed by ethyl acetate wash. Samples were then lyophilized in a SpeedVac Concentrator (Thermo Fischer Scientific). Peptide samples were desalted on Pierce peptide desalting spin column (Thermo Scientific) as per the manufacturer's instructions. After speed-vac concentration, dry samples were suspended in 500 mL of 0.1% formic acid solution. Peptide concentrations were then measured using nanodrop and 20 μg of each sample was aliquoted in autosampler vial for bottom-up proteomics.

All samples were analyzed using two-dimensional (2D) liquid chromatography (LC) on an Ultimate 3000 RSLCnano system (Thermo Fisher Scientific, Waltham, MA) coupled with a Q Exactive Plus mass spectrometer (Thermo Fisher Scientific, Waltham, MA) as previously described[49]. In brief, peptides were separated on an in-house built strong cation exchange (SCX) Luna trap column (5 μm, 150 μm×50 mm; Phenomenex, Torrance, CA) followed by a nanoEase symmetry reversed-phase (RP) C18 trap column (5 μm, 300 μm×50 mm; Waters, Milford, MA) and washed with an aqueous solvent. Proteomics samples were separated and analyzed across three successive SCX fractions of increasing concentrations of ammonium acetate (35 mM, 50 mM, and 500 mM). These fractions were followed by a 100-minute organic gradient (25 nL/min flow rate) to separate peptides across an in-house pulled nanospray emitter analytical column (75 μm×350 mm) packed with C18 Kinetex RP C18 resin (1.7 μm; Phenomenex, Torrance, CA). All MS data were acquired with Thermo Xcalibur (v4.2.47) using the topN method where N could be up to 10.

All MS/MS spectra collected were processed in Proteome Discoverer v2.5 (Thermo Scientific) using SEQUEST HT and Percolator. Spectral data were searched against the *Populus* 717 reference proteome database to which common laboratory contaminants were appended. The following parameters were set up in SEQUEST HT to derive fully tryptic peptides: MS1 tolerance=10 ppm; MS2 tolerance=0.02 Da; missed cleavages=2; Carbamidomethyl (C, +57.021 Da) as static modification; and oxidation (M, +15.995 Da) as dynamic modifications. The percolator FDR threshold was set to 1% at the PSM and peptide levels. FDR-controlled peptides were then quantified according to the chromatographic area-under-the-curve and mapped to their respective proteins. Areas were summed to estimate protein-level abundance.

For qualitative and quantitative analysis of proteome, the protein table was exported from Proteome Discoverer. For qualitative analysis, proteins were filtered to contain high false discovery (<1%) confidence and have at least 2 peptide evidence. For quantitative analysis, proteins were $Log_2$ transformed, LOESS normalized between the biological replicates and mean-centered across all the conditions using InfernoRDN software. Data matrix was then filtered to remove stochastic sampling; all proteins present in $2/3^{rd}$ of biological replicates in any condition were considered valid for quantitative analysis. Missing data were imputed by random numbers drawn from a normal distribution (width=0.3 and downshift=2.8 using Perseus software. Analysis of variance (ANOVA) followed by Tukey's HSD test was performed to identify the significantly changing proteins.

Gas Chromatography-Mass Spectrometry (GC-MS) Metabolite Profiling: Metabolites were extracted from ~150 mg of frozen root powder twice overnight with 2.5 ml of 80% ethanol. Sorbitol (75 μl of 1 mg/ml aqueous solution) was added to the first extract as an internal standard. The two extracts were combined, and a 1 ml aliquot was dried under nitrogen. The dried extracts were silylated to produce trimethysilyl (TMS) derivatives by dissolving in 500 μl of silylation grade acetonitrile (Thermo Scientific, TS20062), followed by addition of 500 μl of N-methyl-N-trimethylsilyltrifluoroacetamide (MSTFA) with 1% trimethylchlorosilane (TMCS) (Thermo Scientific, TS48915) and heated for 1 h at 70° C. After 2 days, 1 μl was injected into an Agilent Technologies 7890A GC coupled to a 5975C inert XL MS configured as previously described (Tschaplinski, T. J. et al., *Biotechnol Biofuels* 5, 71, 2012), except the gas (He) flow was 1.20 ml per minute. Metabolites were identified using a Wiley Registry $10^{th}$ Edition combined with NIST 2014 in addition to a large custom database of TMS-derivatized compounds (Tschaplinski, T. J. et al., *Biotechnol Biofuels* 5, 71, 2012). Metabolite peaks were extracted using key mass-to-charge (m/z) selected ions to minimize interference with co-eluting metabolites and quantified as previously described (Tschaplinski, T. J. et al., *Biotechnol Biofuels* 5, 71, 2012) scaling back to the total ion chromatogram and normalizing to internal standard recovered, volume analyzed, and mass extracted.

What is claimed is:

1. A genetically modified plant, plant cell or plant tissue, comprising an exogenous nucleic acid which comprises a nucleotide sequence encoding a PtrXB38 polypeptide,
   wherein (i) the nucleotide sequence has at least 98% sequence identity to the nucleotide sequence shown in SEQ ID NO: 1, or (ii) the PtrXB38 polypeptide has at least 98% sequence identity to the amino acid sequence shown in SEQ ID NO: 2, and
   wherein the genetically modified plant, plant cell or plant tissue displays an enhanced expression of the PtrXB38 polypeptide and an increase in root development compared to a wild-type plant, plant cell, or plant tissue.

2. The genetically modified plant, plant cell or plant tissue of claim 1, wherein the exogenous nucleic acid is stably integrated into the plant genome.

3. The genetically modified plant, plant cell or plant tissue of claim 1, wherein the nucleotide sequence is operably linked to a heterologous promoter.

4. The genetically modified plant, plant cell or plant tissue of claim 3, wherein the heterologous promoter is a constitutive promoter, an inducible promoter, or a native promoter.

5. The genetically modified plant, plant cell or plant tissue of claim 3, wherein the heterologous promoter is a 35S promoter.

6. The genetically modified plant, plant cell or plant tissue of claim 1, wherein the plant is a monocot or a dicot.

7. The genetically modified plant, plant cell or plant tissue of claim 6, wherein the plant is selected from the group consisting of genera *Eucalyptus, Populus*, and *Salix*.

8. The genetically modified plant, plant cell or plant tissue of claim 7, wherein the plant is *Populus*.

9. The genetically modified plant, plant cell or plant tissue of claim 8, wherein the plant is *Populus trichocarpa*.

10. The genetically modified plant, plant cell or plant tissue of claim 1, wherein the root development comprises adventitious root formation.

11. The genetically modified plant, plant cell or plant tissue of claim 10, wherein the adventitious root formation requires auxin transport and signaling.

12. The genetically modified plant, plant cell or plant tissue of claim 10, wherein the adventitious root formation requires ethylene biosynthesis and signaling.

13. The genetically modified plant, plant cell or plant tissue of claim 1, wherein the enhanced expression of the PtrXB38 polypeptide increases flavonoids in roots.

14. A method of increasing root development in a plant, plant cell or plant tissue, comprising introducing into the plant, plant cell or plant tissue, an exogenous nucleic acid sequence encoding a PtrXB38 polypeptide, thereby obtaining a genetically modified plant, plant cell or plant tissue,
   wherein (i) the nucleotide sequence has at least 98% sequence identity to the nucleotide sequence shown in SEQ ID NO: 1, or (ii) the PtrXB38 polypeptide has at least 98% sequence identity to the amino acid sequence shown in SEQ ID NO: 2, and
   wherein the genetically modified plant, plant cell or plant tissue displays an enhanced expression of the PtrXB38 polypeptide and an increase in root development compared to a wild-type plant, plant cell, or plant tissue.

15. The method of claim 14, wherein the exogenous nucleic acid is stably integrated into the plant genome.

16. The method of claim 14, wherein the nucleotide sequence is operably linked to a heterologous promoter.

17. The method of claim 16, wherein the heterologous promoter is a constitutive promoter or an inducible promoter.

18. The method of claim 16, wherein the heterologous promoter is a 35S promoter.

19. The method of claim 14, wherein the plant is a monocot or a dicot.

20. The method of claim 19, wherein the plant is selected from the group consisting of genera *Eucalyptus, Populus*, and *Salix*.

21. The method of claim 20, wherein the plant is *Populus*.

22. The method of claim 21, wherein the plant is *Populus trichocarpa*.

23. The method of claim 14, wherein the root development comprises adventitious root formation.

24. The method of claim 23, wherein the adventitious root formation requires auxin transport and signaling.

25. The method of claim 23, wherein the adventitious root formation requires ethylene biosynthesis and signaling.

26. The method of claim 23, wherein the enhanced expression of the PtrXB38 polypeptide increases flavonoids in roots.

27. A method of increasing flooding tolerance in a plant or plant tissue comprising enhancing expression of a PtrXB38 polypeptide in the plant, or plant tissue, wherein the PtrXB38 polypeptide has at least 98% sequence identity to the amino acid sequence shown in SEQ ID NO: 2, thereby increasing flooding tolerance in the plant or plant tissue.

28. The method of claim 27, wherein the exogenous nucleic acid is stably integrated into the plant genome.

29. The method of claim 27, wherein the nucleotide sequence is operably linked to a heterologous promoter.

30. The method of claim 29, wherein the heterologous promoter is a constitutive promoter, or an inducible promoter.

31. The method of claim 29, wherein the heterologous promoter is a 35S promoter.

32. The method of claim 27, wherein the plant is a monocot or a dicot.

33. The method of claim 32, wherein the plant is selected from the group consisting of genera *Eucalyptus, Populus*, and *Salix*.

34. The method of claim 33, wherein the plant is *Populus*.

35. The method of claim 34, wherein the plant is *Populus trichocarpa*.

* * * * *